US009697618B2

(12) United States Patent
Nakamura et al.

(10) Patent No.: US 9,697,618 B2
(45) Date of Patent: Jul. 4, 2017

(54) IMAGE PROCESSING APPARATUS, IMAGE PROCESSING METHOD, PROGRAM, AND IMAGE PROCESSING SYSTEM

(71) Applicant: Sony Corporation, Tokyo (JP)

(72) Inventors: Yusuke Nakamura, Chiba (JP); Shinichiro Gomi, Tokyo (JP)

(73) Assignee: Sony Corporation (JP)

( * ) Notice: Subject to any disclaimer, the term of this patent is extended or adjusted under 35 U.S.C. 154(b) by 191 days.

(21) Appl. No.: 14/420,522

(22) PCT Filed: Jul. 2, 2013

(86) PCT No.: PCT/JP2013/068140
§ 371 (c)(1),
(2) Date: Feb. 9, 2015

(87) PCT Pub. No.: WO2014/027522
PCT Pub. Date: Feb. 20, 2014

(65) Prior Publication Data
US 2015/0213619 A1     Jul. 30, 2015

(30) Foreign Application Priority Data

Aug. 17, 2012  (JP) .................................. 2012-180861

(51) Int. Cl.
*G06K 9/00*      (2006.01)
*G06T 7/40*      (2017.01)
(Continued)

(52) U.S. Cl.
CPC ............ *G06T 7/408* (2013.01); *A61B 5/0077* (2013.01); *A61B 5/444* (2013.01); *G06K 9/4652* (2013.01);
(Continued)

(58) Field of Classification Search
CPC ........ A61B 5/0082; A61B 5/442; A61B 5/743; A61B 5/7435; G06F 19/321; G06F 19/345
See application file for complete search history.

(56) References Cited

U.S. PATENT DOCUMENTS 6,215,893 B1 * 4/2001 Leshem ............... A61B 5/0059
                                                           382/128
8,265,417 B2    9/2012 Nakamura et al.
(Continued)

FOREIGN PATENT DOCUMENTS

JP    07-055447 A    3/1995
JP    11-076173 A    3/1999
(Continued)

OTHER PUBLICATIONS

International Search Report from International Publication No. PCT/JP2013/068140 mailed Aug. 6, 2013.

*Primary Examiner* — Tom Y Lu
(74) *Attorney, Agent, or Firm* — Lerner, David, Littenberg, Krumholz & Mentlik, LLP

(57) ABSTRACT

There is provided an image processing apparatus including a feature value calculation unit configured to calculate, as feature values, a polarity related to gradation of a skin image and a scale indicating image areas each having a pixel value that is similar to each other and that are different from surroundings of the image areas, and a feature section extraction unit configured to extract a feature section of the skin image on a basis of the feature values calculated by the feature value calculation unit.

13 Claims, 21 Drawing Sheets

(51) Int. Cl.
*G06T 7/00* (2017.01)
*A61B 5/00* (2006.01)
*G06K 9/46* (2006.01)
*G06T 5/00* (2006.01)

(52) U.S. Cl.
CPC ............ G06T 5/002 (2013.01); G06T 7/0012 (2013.01); G06T 7/0016 (2013.01); *G06T 2207/10024* (2013.01); *G06T 2207/10048* (2013.01); *G06T 2207/10152* (2013.01); *G06T 2207/20028* (2013.01); *G06T 2207/20192* (2013.01); *G06T 2207/30088* (2013.01)

(56) References Cited

U.S. PATENT DOCUMENTS

| | | |
|---|---|---|
| 8,591,414 B2 | 11/2013 | Kitamura et al. |
| 2009/0054744 A1 | 2/2009 | Kitamura et al. |

FOREIGN PATENT DOCUMENTS

| | | | |
|---|---|---|---|
| JP | 2006-305184 A | 11/2006 |
| JP | 2007-130329 A | 5/2007 |
| JP | 2008-293325 A | 12/2008 |
| JP | 2009098925 A | 5/2009 |
| JP | 2010-119431 A | 6/2010 |
| JP | 2011-118671 A | 6/2011 |

* cited by examiner

FIG. 10

| DETECTION TARGET | POLARITY | SCALE | LIGHT SOURCE |
|---|---|---|---|
| PORE | BLACK | 0.1 to 0.3 mm | WHITE |
| PIMPLE | WHITE | 0.5 to 1.0 mm | WHITE |
| IMPURITY IN PORE | WHITE(GRAY SCALE), ORANGE, OR GREEN | 0.2 to 0.5 mm | NEAR ULTRAVIOLET |

IMAGE PROCESSING APPARATUS, IMAGE PROCESSING METHOD, PROGRAM, AND IMAGE PROCESSING SYSTEM

CROSS-REFERENCE TO RELATED APPLICATION

The present application is a national phase entry under 35 U.S.C. §371 of International Application No. PCT/JP2013/068140 filed Jul. 2, 2013, published on Feb. 20, 2014 as WO 2014/027522 A1, which claims priority from Japanese Patent Application No. JP 2012-180861 filed in the Japanese Patent Office on Aug. 17, 2012.

TECHNICAL FIELD

The present technique relates to an image processing apparatus, an image processing method, a program, and an image processing system that enable accurate detection of feature sections from a skin image.

BACKGROUND ART

Hitherto, during skin counseling and the like, various types of measurement is conducted on a skin of a user and various pieces of advice is given based on measurement results. For example, sizes of the pores are measured to select a cosmetic in accordance with the sizes of the pores and to check a therapeutic effect of a treatment and the like for reducing the size of the pores.

Regarding the measurement of the pores, for example, in Patent Literature 1, a smoothing image is subtracted from an original image and binarization is performed on the image, on which subtraction has been performed, so as to divide the image into areas indicating the pores and other areas to measure the number, size, and the like of the areas indicating the pores.

CITATION LIST

Patent Literature

Patent Literature 1: JP H7-55447A

SUMMARY OF INVENTION

Technical Problem

Incidentally, edge components and texture components that become hindering factors in detecting pores are anticipated to be included in an image in which a smoothing image has been subtracted from an original image. Accordingly, when binarization is performed on an image on which the subtraction, a concern is encountered in that the areas indicating the pores and the areas indicating the edge components and the texture components cannot be distinguished from each other such that the pores serving as feature sections cannot be detected in an accurate manner.

Furthermore, not limited to pores, if pimples such as acne can be detected as well as the feature sections when measuring the skin, various pieces of advice and the like can be given in an appropriate manner in accordance with the skin condition.

Accordingly, an object of the present technique is to provide an image processing apparatus, an image processing method, a program, and an image processing system that are capable of accurately detecting feature sections from a skin image.

According to a first aspect of the present disclosure, there is provided an image processing apparatus including a feature value calculation unit configured to calculate, as feature values, a polarity related to gradation of a skin image and a scale indicating image areas each having a pixel value that is similar to each other and that are different from surroundings of the image areas, and a feature section extraction unit configured to extract a feature section of the skin image on a basis of the feature values calculated by the feature value calculation unit.

Solution to Problem

In the present technique, a brightness information separation processing is performed on a skin image, a skin-surface reflection of which has been removed by, for example, configuring a light source and a polarizing filter that has been provided in an imagining unit to have an orthogonal relationship with each other, so as to acquire a global brightness information that indicates the structural components of the skin. Calculation of the feature values is performed using the global brightness information. For example, polarities related to gradation of the skin image and scales indicating image areas having pixel values that are similar to each other and that are different from the surroundings of the image areas are calculated as the feature values. Furthermore, intensities indicating signal differences between the image areas that have pixel values similar to each other and the surroundings of the image areas may be further calculated as the feature values. Based on such feature values, for example, at least either of the pores, pimples, blemishes, and impurities in pores that are feature sections of the skin image are extracted. Furthermore, on the basis of the extraction result of the feature sections, the feature sections being feature values that satisfy extraction conditions set in advance, a statistic is calculated to generate information related to at least either of a number, a size, and a color density of the feature sections.

Furthermore, a melanin analysis unit that performs analysis of melanin is provided and extraction of the feature sections is performed with the feature values that have been calculated on the basis of the skin image and with the melanin analysis result of the skin image. For example, extraction of the feature sections is performed with the feature values that have been calculated on the basis of the skin image taken with a white light and with the melanin analysis result of the skin image and the like that has been taken with a red light and a near infrared light, or a ultraviolet light. Furthermore, an image positioning unit that matches the position of the skin image of the past and the position of the skin image of the present, for example, to match the feature sections is provided, and with matching of the feature sections performed with the second feature value indicating polarities of the intensity change, matching of the positions of the skin images is performed so that the corresponding feature sections of the skin image of the past and skin image of the present are matched. Furthermore, when the number of corresponding feature sections is equivalent to or smaller than a predetermined number, a piece of advice is presented for moving an imaging area so that the positions of the corresponding feature sections of the second skin image are positioned at the positions of the corresponding feature section of the first skin image.

According to a second aspect of the present disclosure, there is provided an image processing method including the steps of calculating, as feature values, a polarity related to gradation of a skin image and a scale indicating image areas each having a pixel value that is similar to each other and that are different from surroundings of the image areas, and extracting a feature section of the skin image on a basis of the calculated feature values.

According to a third aspect of the present disclosure, there is provided a program for causing a computer to execute a skin image processing, the program causing the computer to execute calculating, as feature values, a polarity related to gradation of a skin image and a scale indicating image areas each having a pixel value that is similar to each other and that are different from surroundings of the image areas, and extracting a feature section of the skin image on a basis of the calculated feature values.

Note that the program of the present technology is a program that can be provided using a storage medium and a communication medium that is provided to a general-purpose computer that can execute various program codes in a computer-readable form, for example, a storage medium such as an optical disc, a magnetic disk, a semiconductor memory or a communication medium such as a network. By providing the program in the computer-readable form, a process according to the program is realized on a computer.

According to a fourth aspect of the present disclosure, there is provided an image processing system including an imaging device, and an information device. The imaging device is provided with an imaging unit configured to generate a skin image. One of the imaging device and information processing device is provided with a feature value calculation unit configured to calculate, as feature values, a polarity related to gradation of a skin image and a scale indicating image areas each having a pixel value that is similar to each other and that are different from surroundings of the image areas, a feature section extraction unit configured to extract a feature section of the skin image on a basis of the feature values calculated by the feature value calculation unit, and a presentation unit configured to present an extraction result of the feature section.

Advantageous Effects of Invention

According to the present technique, polarities related to gradation of the skin image and scales indicating image areas having pixel values that are similar to each other and that are different from the surroundings of the image areas are calculated as feature values, and on the basis of the feature values, the feature sections of the skin image are extracted. Accordingly, the pores, the principles, and the like of the skin can be accurately detected as the feature sections and, thus, various pieces of advice and the like can be given in an appropriate manner in accordance with the skin condition. Note that the effects described in the present description are only exemplifications and the effects are not limited to those described in the present description and, further, there may be additional effects.

BRIEF DESCRIPTION OF DRAWINGS

FIG. 10 is a diagram illustrating a relationship between detected feature sections, light sources, and extraction conditions of the feature sections.

DESCRIPTION OF EMBODIMENTS

Figure 1:
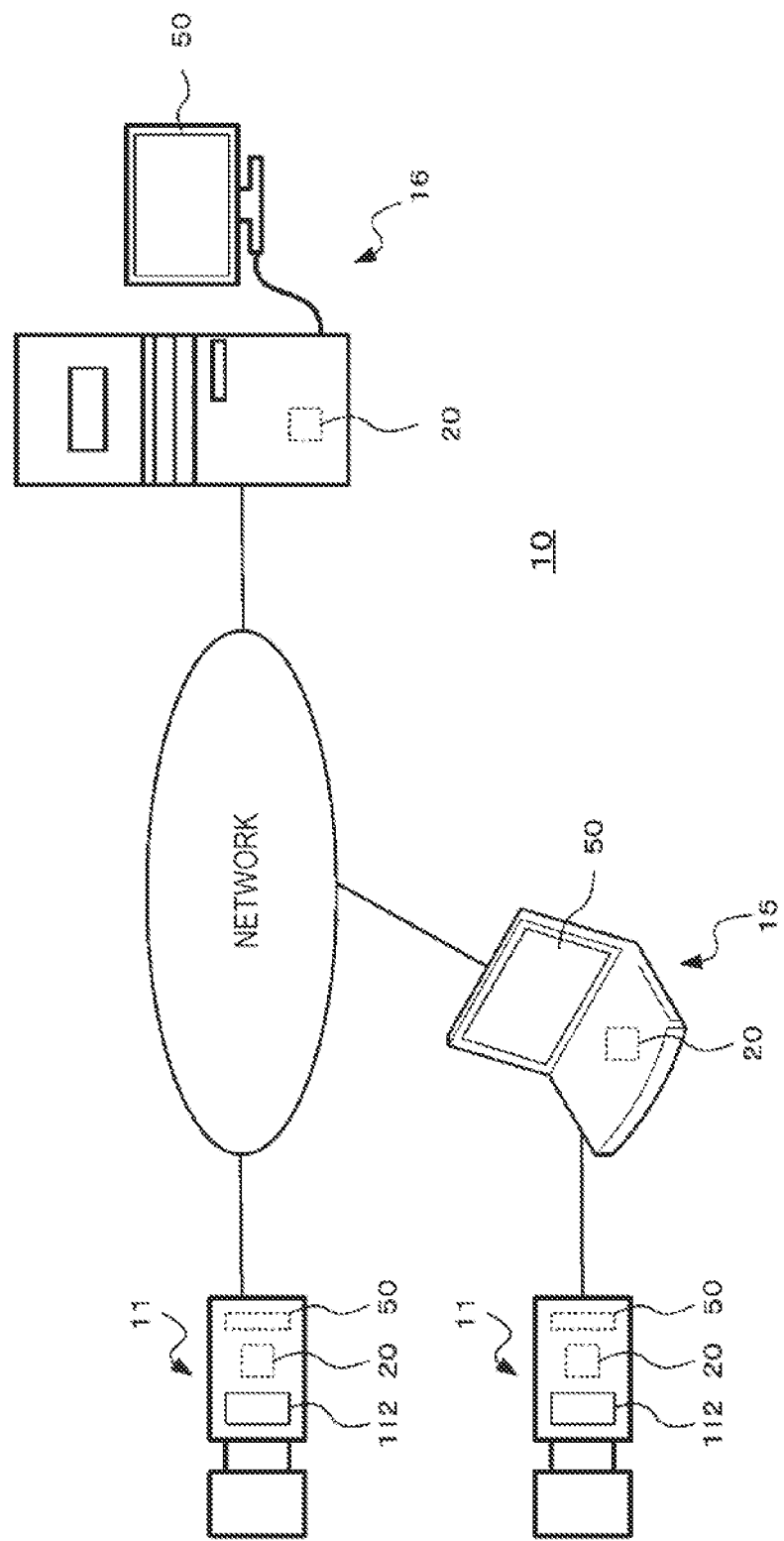
FIG. 1 is a diagram exemplifying a configuration of an image processing system.

Hereinafter, embodiments of the present technique will be described. Note that the description will be given in the following order.
1. Image processing system
2. First embodiment
2-1. Configuration of first embodiment
2-2. Operation of first embodiment
3. Second embodiment
3-1. Configuration of second embodiment
3-2. Operation of second embodiment
4. Third embodiment
4-1. Configuration of third embodiment
4-2. Operation of third embodiment
<1. Image Processing System>
FIG. 1 exemplifies a configuration of an image processing system of the present technique. An image processing system 10 is constituted by employing a piece of equipment (hereinafter referred to as "an imaging device") 11 that has an imaging function, information processing devices 15 and 16, and the like. The imaging device 11 and the information processing device (a personal computer device, for example) 15 can be directly coupled to each other through a wired or wireless transmission path. Furthermore, the imaging device 11 and the information processing device (a server device, for example) 16 can be coupled to each other through a public telecommunication network and the like.

The imaging device 11 includes an imaging unit 112 that generates a captured image of the skin. An image processing apparatus 20 detecting feature sections of the skin is provided in either of the imaging device 11 and the information processing devices 15 and 16. The image processing apparatus 20 includes a feature value calculation unit and a feature section extraction unit. The feature value calculation unit calculates, as feature values, polarities related to gradation and scales indicating pixel areas having pixel values that are similar to each other and that are different from the surroundings of the pixel areas from the captured image of the skin (hereinafter, referred to as a "skin image"). The feature section extraction unit extracts feature sections of the skin on the basis of the calculated feature values. Furthermore, a presentation unit 50 that presents an extraction result of the feature sections of the skin is provided in either of the imaging device 11 and the information processing device 15 and 16. Note that the skin image used to detect the feature sections of the skin with the image processing apparatus 20 is not limited to the skin image that is output from the imaging unit 112 and maybe a skin image that has been generated in the imaging unit 112 and that has been stored in a recording medium or the like.

<2. First Embodiment>

In the first embodiment, a case in which feature sections, such as pores and the like, are detected from a skin image with the image processing apparatus 20 will be described.

Figure 2:
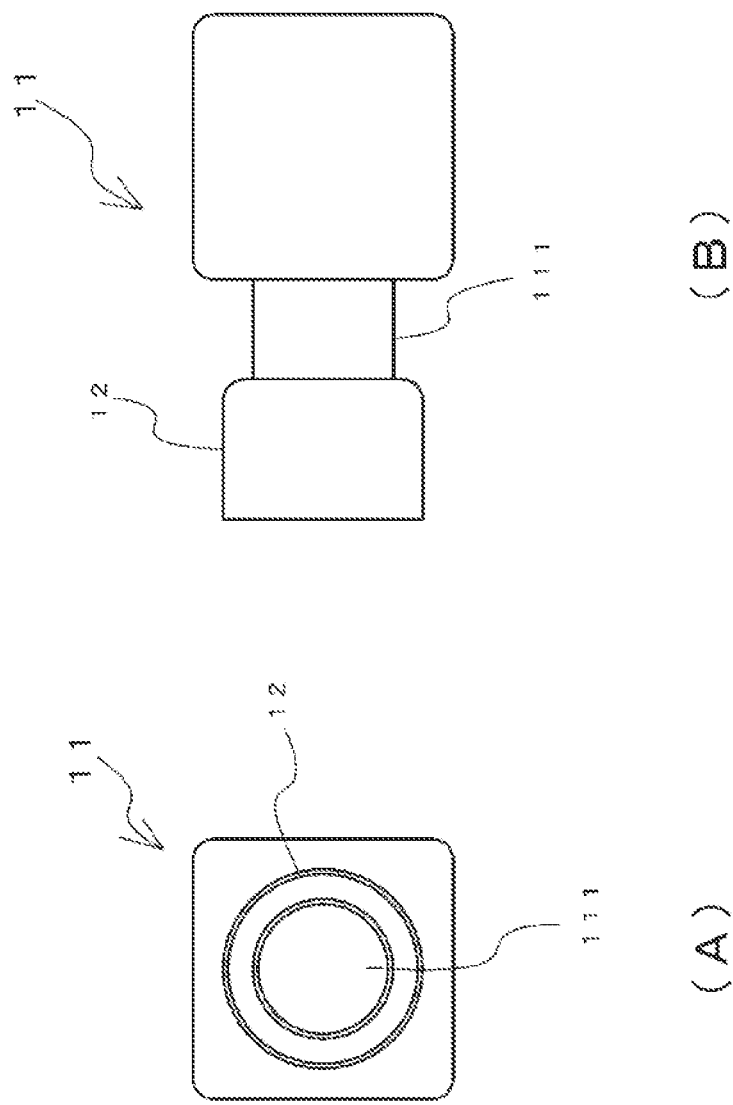
FIG. 2 includes diagrams illustrating a configuration of an imaging device in a schematic manner.
Figure 3:
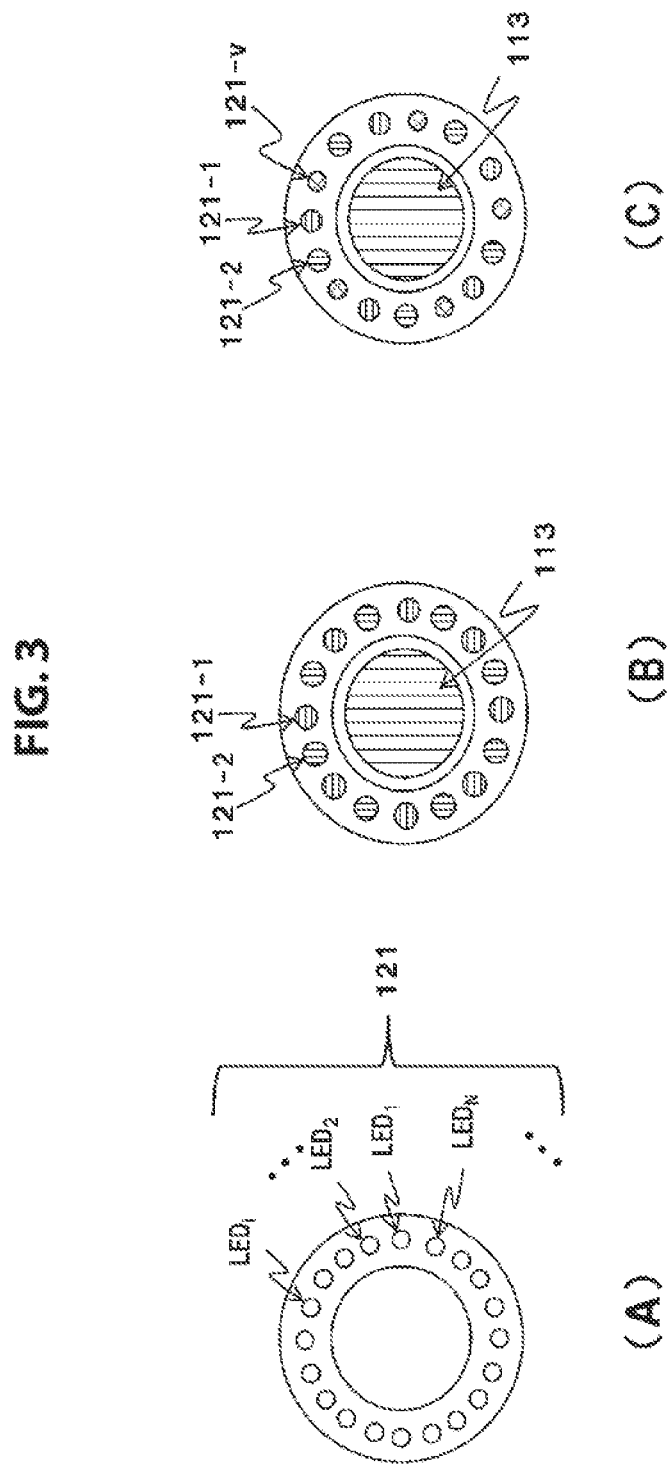
FIG. 3 includes diagrams each illustrating an exemplification of light sources of an attachment.

FIG. 2 illustrates, in a schematic manner, a configuration of the imaging device that takes an image of the skin. Note that FIG. 2(A) is a front view of the imaging device 11 and FIG. 2(B) is a side view of the imaging device 11. An attachment 12 is provided at the distal end of a lens barrel 111 of the imaging device 11. Furthermore, the attachment 12 may be integrally formed with the lens barrel 111 or may be configured so as to be attachable to and detachable from the lens barrel 111. As illustrated in FIG. 3(A), a plurality of light sources 121 (light emitting diodes (LEDs) 1 to n, for example) that constitute an illumination unit are arranged in a ring shape in the attachment 12. A white LED is preferable as the light source. When a skin image of an internal reflection component is to be obtained after removal of a skin-surface reflection component has been performed, as illustrated in FIG. 3(B), white LEDs 121-1 provided with polarizing filters each having a predetermined polarization plane and white LEDs 121-2 provided with a polarizing filter having a polarization plane that is, for example, orthogonal to the predetermined polarization planes are provided. Furthermore, as illustrated in FIG. 3(C), impurities in pores serving as feature sections may be detected with near-ultraviolet light LEDs 121-v.

Figure 4:
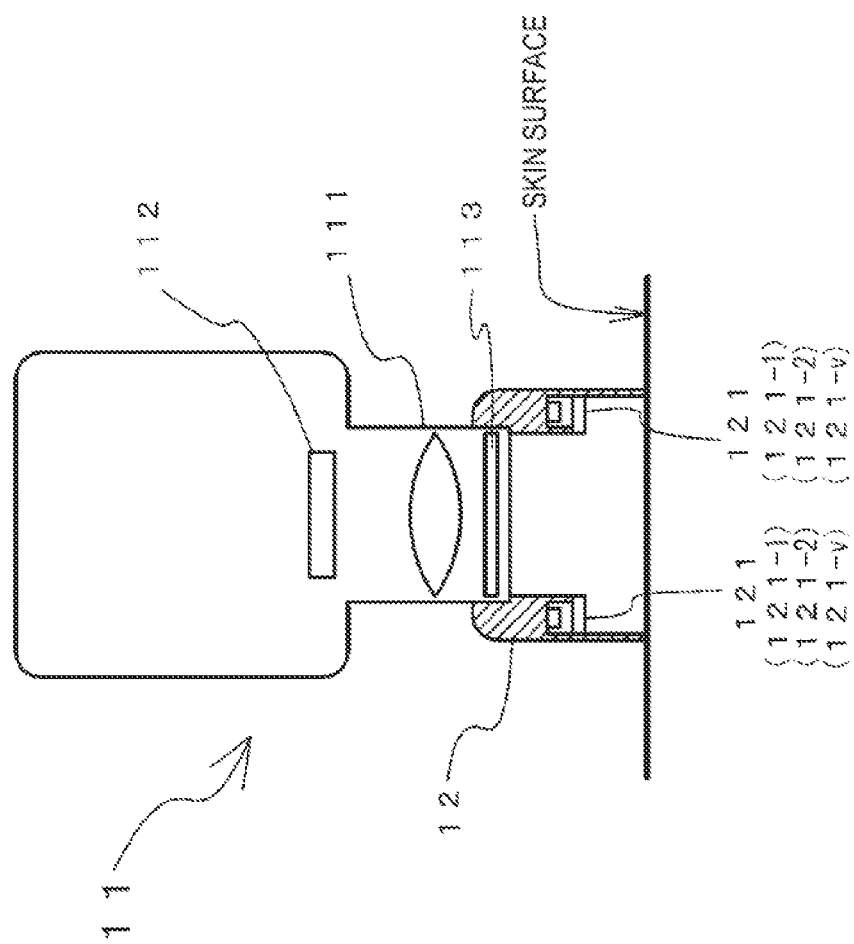
FIG. 4 is a diagram illustrating a position of the imaging device when an image is taken.

As illustrated in FIG. 4, for example, the imaging device 11 provided with the attachment 12 captures a skin image by being in close contact with the skin. Furthermore, when the light sources that are provided with the polarizing filter are used, a polarizing filter 113, the polarization plane of which is orthogonal to the predetermined polarization plane, is provided in the optical path extending to the imaging unit 112. Since the polarizing filter is provided in the above described manner, by taking an image after turning on the white LEDs 121-1, an image, the skin-surface reflection component of which has been removed, can be obtained, and by taking an image after turning on the white LEDs 121-2, an image, the skin-surface reflection component of which has not been removed, can be obtained.

[2-1. Configuration of First Embodiment]

Figure 5:
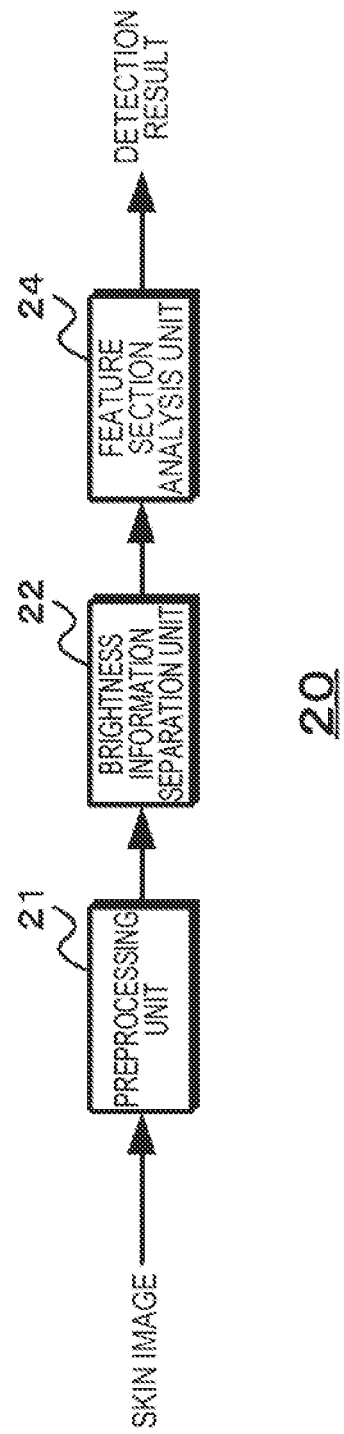
FIG. 5 is a diagram illustrating a configuration of a first embodiment of the image processing apparatus.

FIG. 5 illustrates a configuration of the first embodiment of an image processing apparatus. The image processing apparatus 20 includes a preprocessing unit 21, a brightness information separation unit 22, and a feature section analysis unit 24.

The preprocessing unit 21 acquires a skin image and performs preprocessing. The preprocessing unit 21 performs contrast enhancement processing to the acquired brightness information of the skin image to greatly emphasize the shadows. Histogram equalization processing, for example, is employed as the method of performing the contrast enhancement processing. Furthermore, when noise stands out, noise removal may be performed before the contrast enhancement, and when shades stand out, shading compensation may be performed before the contrast enhancement.

The brightness information separation unit 22 separates the brightness information that has been obtained by the preprocessing unit 21 into global brightness information and local brightness information. The global brightness information is information that indicates lighting components included in the image and structural components of the skin. Furthermore, the local brightness information is information that indicates detailed patterns of the skin, such as texture.

In separating the brightness information, for example, the global brightness information may be separated by performing a low pass processing on the input brightness information and, accordingly, the separation method disclosed in JP 2009-98925A may be employed. In the above separation method, brightness information $f_G'$ (see expression (1)) is generated by performing a low-pass filtering processing on brightness information (input brightness information) $f_{in}^W$ that has been acquired. Furthermore, low amplitude components of the differential between the input brightness information $f_{in}^W$ and the brightness information $f_G'$ are solely set as local brightness information $f_L^W$. In such a case, when a simple low-pass filtering processing is performed on a portion with high edge intensity, an intense edge will be included in the local brightness information. Accordingly, local brightness information $f_L^W$ is generated by extracting only the low amplitude components by using function C that suppresses high amplitude components (see expression (2)). Moreover, global brightness information $f_G^W$ is generated by calculating the differential between the input brightness information $f_{in}^W$ and the local brightness information $f_L^W$ (see expression (3)).

[Math. 1]

$$f_G'(x,y) = lpf \otimes f_{in}^W(x,y) \tag{1}$$

$$f_L^W(x,y) = C(f_{in}^W(x,y) - f_G'(x,y)) \tag{2}$$

$$f_G^W(x,y) = (f_{in}^W(x,y) - f_L^W(x,y)) \tag{3}$$

Figure 6:
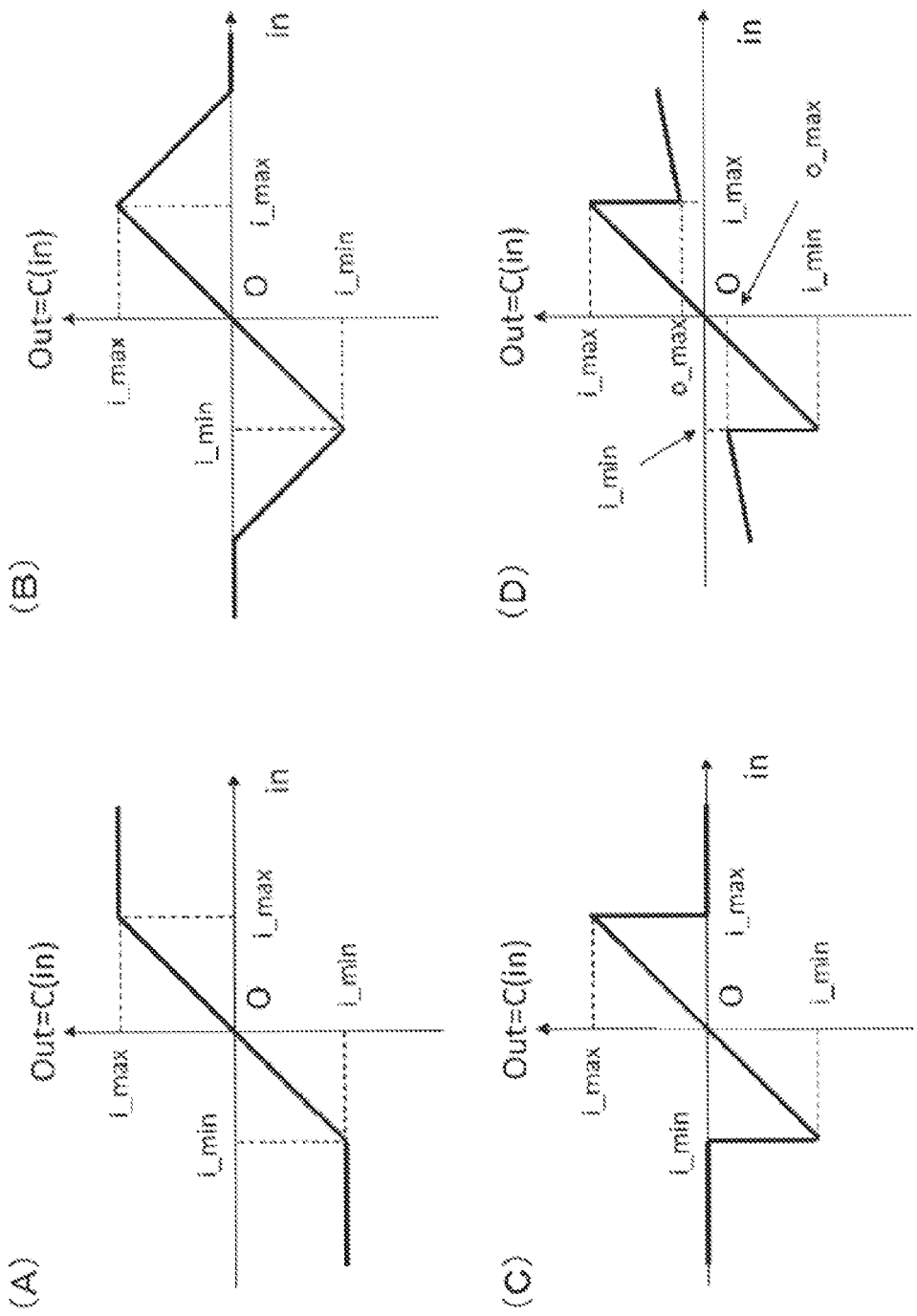
FIG. 6 includes diagrams exemplifying function C.

FIG. 6 exemplifies function C. In function C, processing that suppresses amplitude is performed on signals whose amplitudes are not included in the range of "i_min-i_max". Note that FIGS. 6(A) to 6(D) exemplify function C having different amplitude suppression characteristics.

Furthermore, in another separating method, the limitation of amplitude is performed by applying function C to the differentials between the input brightness information and each of the pieces of brightness information on which filter processing has been performed by a plurality of low-pass filters having different pass frequency bands. The global brightness information can be generated using the local brightness information that is an integration of the brightness information on which the limitation of amplitude has been performed.

For example, the brightness information $f_G{}'$ is generated by performing the low-pass filtering processing on the input brightness information $f_{in}{}^W$ with three low-pass filters having different pass frequency bands (see expression (4)). Note that in expressions (4) and (5), S, M, and L indicate the number of taps of the low-pass filters, and the bands of the low-pass filters become narrower in this order. Subsequently, with function C, only the low amplitude components are extracted from the differential between the input brightness information $f_{in}{}^W$ and brightness information $f_{Gj}{}^W$ to generate brightness information $f_{Lj}{}^W$ (see expression (5)). Furthermore, the local brightness information $f_L{}^W$ is generated by integrating the brightness information $f_{Lj}{}^W$ with the blended ratios $BR_s$ and $BR_M$ corresponding to the edge intensities (see expression (6)). The global brightness information $f_G{}^W$ may be generated from expression (3) with the local brightness information $f_L{}^W$ generated as above.

[Math. 2]

$$f_{Gj}'(x,y) = lpf_j \otimes f_{in}{}^W(x,y) \quad (j=S,M,L) \tag{4}$$

$$f_{Lj}{}^W(x,y) = C(f_{in}{}^W(x,y) - f_{Gj}'(x,y)) \quad (j=S,M,L) \tag{5}$$

$$f_L{}^W(x,y) = BR_S \times f_{L_S}{}^W(x,y) + (1-BR_S) \times (BR_M \times f_{L_M}{}^W(x,y) + (1-BR_M) \times f_{L_L}{}^W(x,y)) \tag{6}$$

Figure 7:
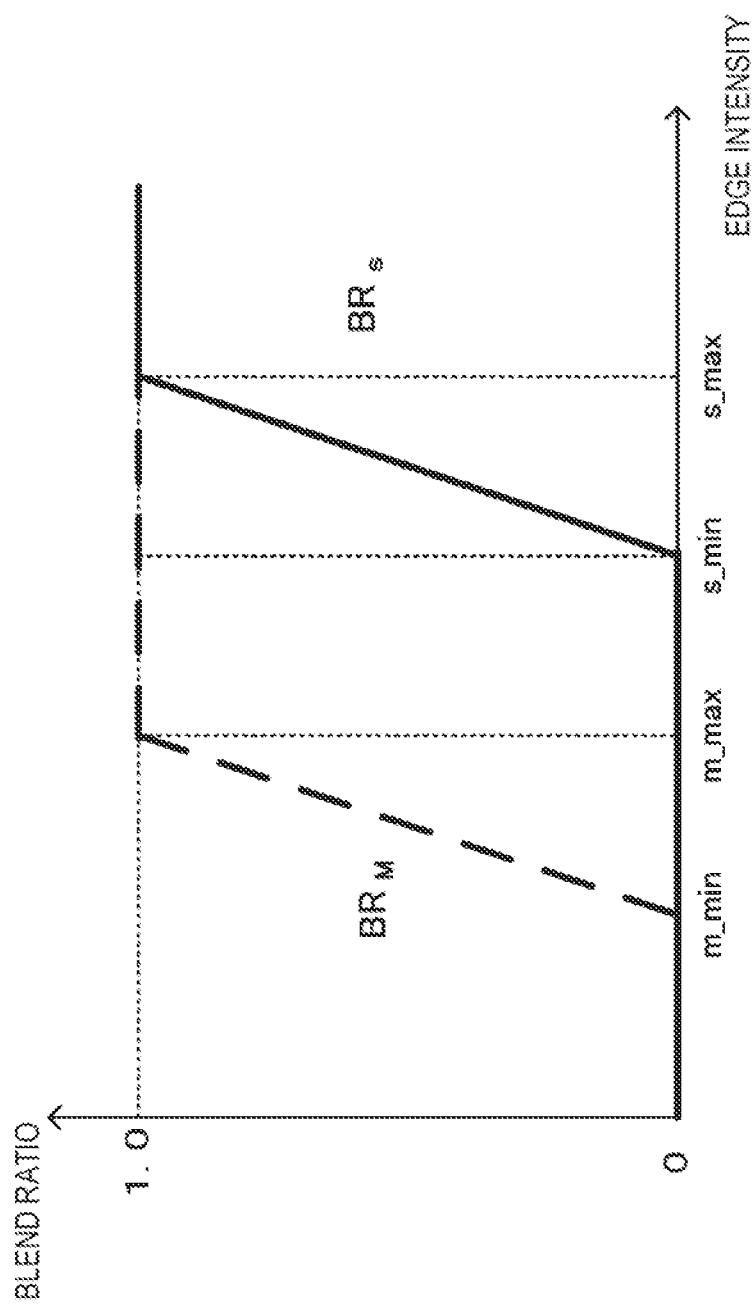
FIG. 7 is a diagram exemplifying blend ratios $BR_s$ and $BR_M$.

FIG. 7 exemplifies the blended ratios $BR_s$ and $BR_M$. The ratios of the blend ratio $BR_s$ and the blend ratio $BR_M$ are both high when the edge intensity is high. The ratio of the blend ratio $BR_M$ is higher than that of the blend ratio $BR_s$ when the edge intensity is moderate. The ratio of the blend ratio $BR_s$ and the blend ratio $BR_M$ are both low when the edge intensity is low.

Note that the separation of the brightness information is not limited by the methods described above and, for example, a known edge-preserving smoothing filter such as, for example, a bilateral filter may be applied as the low-pass filter.

Figure 8:
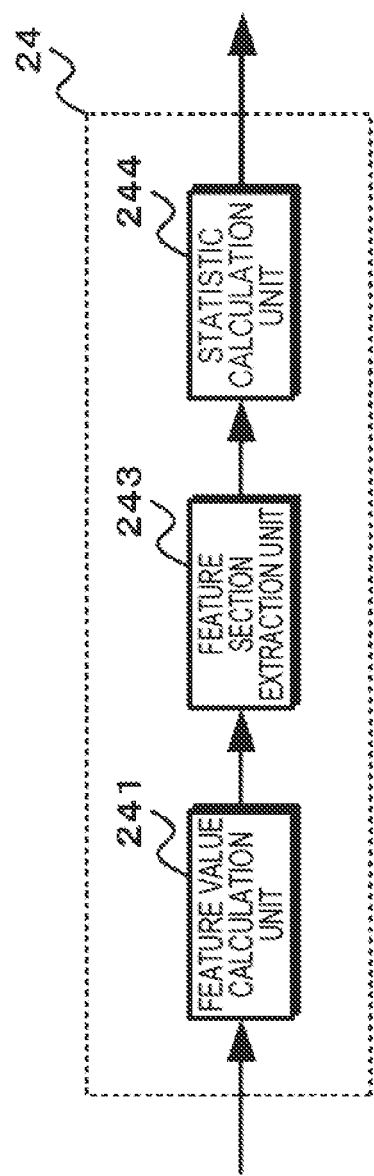
FIG. 8 is a diagram illustrating a configuration of a feature section analysis unit.

The feature section analysis unit 24 calculates the feature values from the skin image and, on the basis of the calculated feature values, analyzes the feature sections of the skin. FIG. 8 illustrates a configuration of the feature section analysis unit 24. The feature section analysis unit 24 includes a feature value calculation unit 241, a feature section extraction unit 243, and a statistic calculation unit 244.

The feature value calculation unit 241 calculates the feature values. The feature value calculation unit 241 calculates the feature values using the global brightness information generated in the brightness information separation unit 22, for example. The feature value calculation unit 241 calculates, as feature values, polarities related to gradation of the skin image, and scales indicating pixel areas having pixel values that are similar to each other and that are different from the surroundings of the pixel areas. Furthermore, the feature value calculation unit 241 may further calculate, as feature values, intensities indicating signal differences between the image areas that have pixel values similar to each other and the surroundings of the image areas.

Calculation of the feature values will be described next. Calculation of the feature points is performed using an image feature extraction technique. Techniques such as Speeded Up Robust Features (SURF) and Scale Invariant Feature Transform (SIFT) are known as image feature extraction techniques.

For example, in Speeded Up Robust Feature (SURF), the feature points (white circles and black circles) in the image are selected in the following manner. Specifically, the feature points in the image are detected by searching points having the maximum matrix value of the Hessian matrix while the standard deviation σ of the Gaussian function is changed. In order to increase speed while calculating the matrix value of the Hessian matrix, computation of expression (7) that employs an approximation filter is performed. Note that in expression (7), $D_{xx}$, $D_{yy}$, and $D_{xy}$ indicate convolutions of the image based on the second order Gaussian derivatives that are components of the Hessian matrix calculated using a box filter. Furthermore, the filter size corresponds to the Gaussian standard deviation and, for example, a filter size of 9×9 corresponds to σ=1.2.

[Math. 3]

$$\det(H_{approx}) = D_{xx}D_{yy} - (0.9D_{xy})^2 \tag{7}$$

The feature value calculation unit 241 calculates, as feature values, scales indicating pixel areas having pixel values that are similar to each other and that are different from the surroundings of the pixel areas, in other words, the feature value calculation unit 241 calculates, as feature values, scales in which the matrix value calculated in expression (7) becomes maximum. Furthermore, the feature value calculation unit 241 sets the polarities related to gradation of the skin image as the feature values, in other words, the feature value calculation unit 241 sets the Laplacian value of the feature points from which the feature values has been calculated as the feature values. Furthermore, the feature value calculation unit 241 may include, in the feature values, the intensities indicating signal differences between the image areas that have pixel values similar to each other and the surroundings of the image areas, such as the maximum value of the matrix values that have been calculated in expression (7). Note that the feature value calculation unit 241 may use the other feature extraction technique described above to calculate the feature values.

The feature section extraction unit 243 extracts the feature sections on the basis of the feature values that have been obtained by the feature value calculation unit 241. For example, when the pore portions are extracted as the feature sections, the feature section extraction unit 243 sets Laplacian to "1" as the extraction condition. This is because the above matches with the characteristics of the pores since the Lapacian indicates the polarities related to gradation of the skin image and the black pixels are surrounded by the white pixels when the Laplacian is "1". Furthermore, the feature section extraction unit 243 limits the scales that indicate the pixel areas having pixel values that are similar to each other and that are different from the surroundings of the pixel areas. It is known that the size of a pore is about 0.1 mm to 0.3 mm. Accordingly, the feature section extraction unit 243 sets an extraction condition that the scale of the feature values obtained by the feature value calculation unit 241 to correspond to the size of the pores.

Furthermore, the feature section extraction unit 243 may limit the intensities. A feature that is considered to be an area where the pores stand out needs a certain amount of signal intensity (contrast difference) with respect to the other areas. Accordingly, the feature section extraction unit 243 sets, as an extraction condition, an intensity (a matrix value) that is capable of extracting pores and the like that stands out.

By extracting the feature points that satisfy all of the extraction conditions that are set as above as the feature sections of the skin, the feature section extraction unit 243 will be capable of extracting only the pore areas from the skin image. Note that as described later, the extraction conditions may be changed to extract pimples and the like as feature sections of the skin.

The static calculation unit 244 calculates statistics of the feature sections that have been extracted by the feature section extraction unit 243. For example, when the pores are extracted as the feature sections, statistic calculation unit 244 measures the number of extracted feature sections and calculates the number of pores. Furthermore, the statistic calculation unit 244 calculates an average value of the scales of the extracted feature sections to obtain a statistic of the size of the pores from the average value. Furthermore, the statistic calculation unit 244 calculates an average value of the intensities (Hessian value, for example) of the extracted feature sections to set a color density of the pores. Furthermore, not limited to the average value, the statistic calculation unit 244 may calculate a maximum value, a variance, and the like. Furthermore, classification of the size and the color of the pores may be performed and a class value may be calculated for each class. Furthermore, not limited to the pores, the statistic calculation unit 244 may calculate a statistic of the pimples and the like in a similar manner. Moreover, the statistic calculation unit 244 may obtain a rate of the areas with high melanin index.

The presentation unit 50 that is provided in the imaging device 11, the information processing device 15, or the like presents the analysis result of the feature section analysis unit 24 to a user. For example, the presentation unit 50 displays the statistic that has been calculated in the feature section analysis unit 24 on a screen.

[2-2. Operation of First Embodiment]

Figure 9:
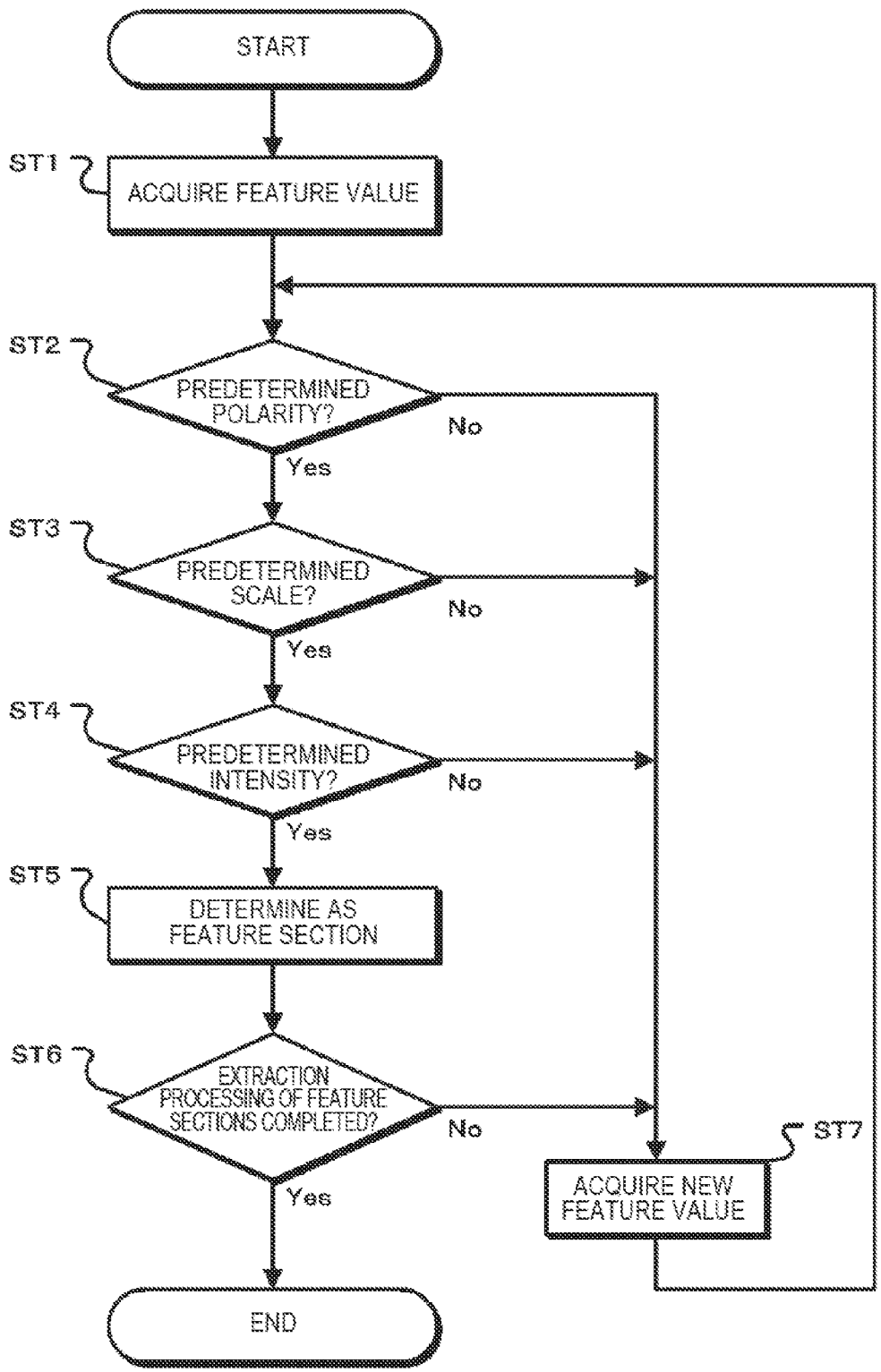
FIG. 9 is a flow chart illustrating an operation extracting feature sections.

An operation of the first embodiment of the image processing apparatus will be described next. FIG. 9 is a flowchart illustrating an operation extracting the feature sections. In step ST1, the image processing apparatus 20 acquires a feature value. The image processing apparatus 20 acquires a feature value that has been calculated using the global brightness information and that indicates, for example, a polarity related to gradation of the skin image, a scale indicating pixel areas having pixel values that are similar to each other and that are different from the surroundings of the pixel areas, and an intensity (a contrast difference), and proceeds to step ST2.

In step ST2, the image processing apparatus 20 discriminates whether the feature value has a predetermined polarity. When the feature value indicates a polarity of the extracted feature sections, for example, when the Laplacian is "1" and the feature value matches the characteristics of the pores, then the image processing apparatus 20 proceeds to step ST3. Furthermore, the image processing apparatus 20 proceeds to step ST7 when the feature value does not indicate the polarity of the feature sections.

In step ST3, the image processing apparatus 20 discriminates whether the feature value is of a predetermined scale. When the feature value indicates the scale of the extracted feature sections, for example, when the scales indicated in the feature value is a scale that correspond to the pores, then the image processing apparatus 20 proceeds to step ST4. Furthermore, the image processing apparatus 20 proceeds to step ST7 when the feature value does not indicate the predetermined scale.

In step ST4, the image processing apparatus 20 discriminates whether the feature value has a predetermined intensity. When the feature value indicates the intensity of the extracted feature section, for example, when the intensity indicated in the feature value is an intensity that corresponds to the contrast difference between the pore portions and the skin portion, then the image processing apparatus 20 proceeds to step ST5. Furthermore, when the feature value does not indicate the predetermined intensity, for example, when the intensity indicated in the feature value is lower than the contrast difference between the pore portions and the skin portion, then the image processing apparatus 20 proceeds to step ST7.

In step ST5, the image processing apparatus 20 determines that the feature value is a feature section. For example, the when the feature value satisfies the extraction conditions of the pores in step ST2 to step ST4, the image processing apparatus determines that the feature value is a feature section indicating the pores and proceeds to step ST6.

In step ST6, the image processing apparatus 20 discriminates whether the extraction processing of the feature sections have been completed. If an area of the feature value that has not been determined whether it is a feature section or not remains, the image processing apparatus 20 proceeds to step ST7, and if no such feature value remains, the image processing apparatus 20 ends the operation of extracting the feature sections.

In step ST7, the image processing apparatus 20 acquires a new feature value. The image processing apparatus 20 acquires a feature value that has not been determined whether it is a feature section and returns to step ST2.

Note that in the operation of extracting the feature sections, the order in which the polarities, the scales, and the intensities are determined is not limited to the order illustrated in FIG. 9 but may be ordered in a different manner. Furthermore, the feature sections may be extracted without performing any determination of the intensity.

By performing such processing, the image processing apparatus 20 extracts the pore portions from the skin image in an accurate manner. Furthermore, when an extraction result of the feature sections is presented on the presentation unit 50, the result is presented in a manner that the user can easily understand.

Furthermore, when pimples and impurities in pores are to be detected as feature sections, the wavelength of the light source and the extraction conditions of the feature points may be switched so that not only the pores but also the pimples, the impurities in pores, and the like can be detected. FIG. 10 illustrates the relationship between the extracted feature sections, the light source, and the extraction conditions. For example, when the pores are detected, a white light source is used. The extraction conditions are set such that polarities indicate features that are surrounded by pixels with high brightness and such that the range of the scale is about 0.1 to 0.3 mm. When pimples are detected, a white light source is used. The extraction conditions are set such that polarities indicate features that are surrounded by pixels with low brightness and such that the range of the scale is about 0.5 to 1.0 mm. When impurities in pores are detected, a near-ultraviolet light source is used. It is known that a portion with sebum emits green light with near-ultraviolet light and that a portion with porphyrin created by acne bacteria emits orange light with near-ultraviolet light. Accordingly, the extraction conditions are set such that polarities indicate features that are surrounded by pixels with low brightness when the skin image is gray scaled, such that polarities indicate a green and an orange light with near-ultraviolet light, and such that the range of the scale is about 0.2 to 0.5 mm.

Figure 11:
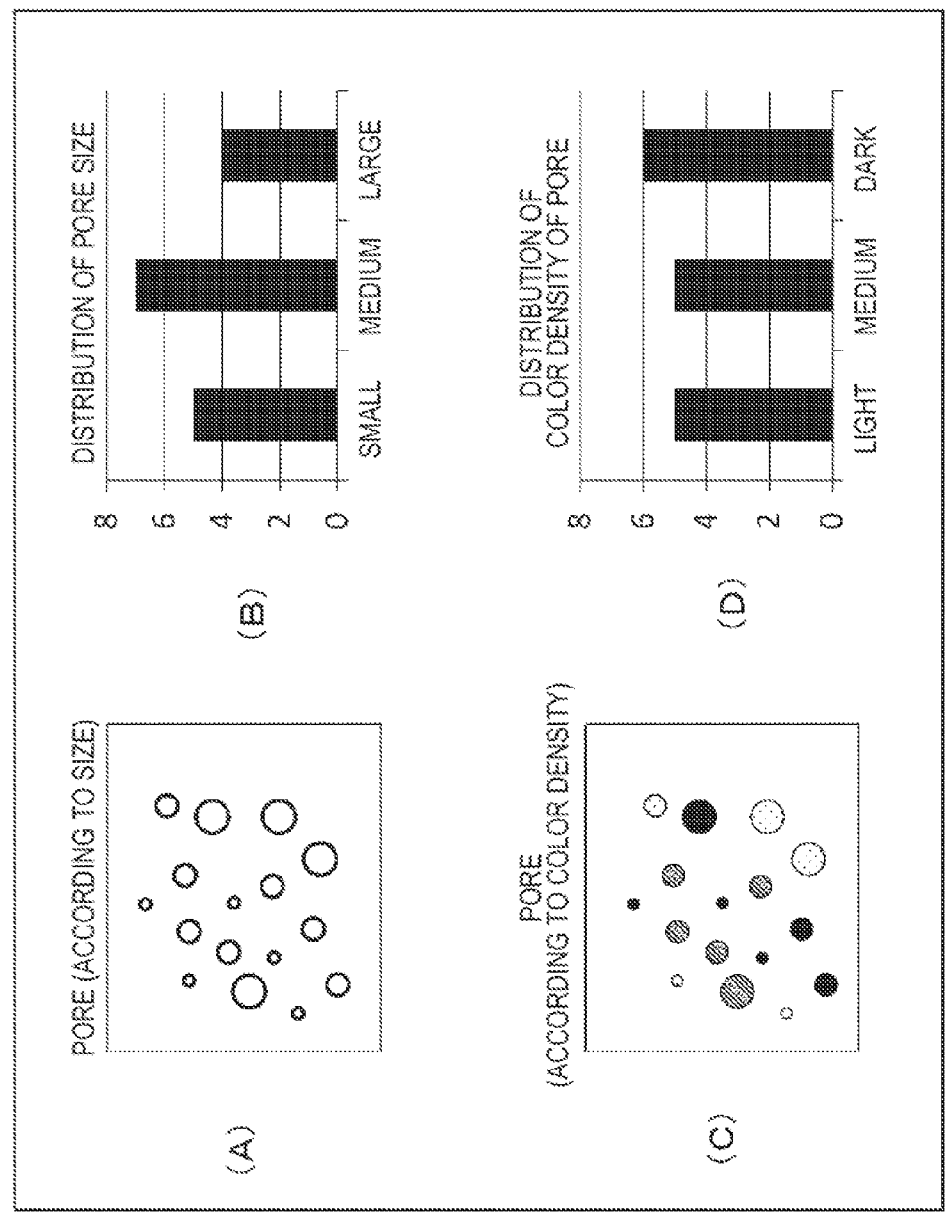
FIG. 11 is a diagram exemplifying an operation of a presentation unit.

FIG. 11 exemplifies an operation of the presentation unit. FIG. 11(A) illustrates a state in which the pores are plotted on the skin image according to their sizes, for example, and FIG. 11(B) is a distribution (a histogram) of the sizes of the pores displayed according to their sizes. FIG. 11(C) illustrates a state in which the pores are plotted on the captured image according to their color densities. Furthermore, FIG. 11(D) is a distribution (a histogram) of the color densities of the pores displayed according to their color densities. As described above, the extraction result of the feature sections are presented on the presentation unit 50 in a manner that can be easily understood by the user.

<3. Second Embodiment>

Figure 12:
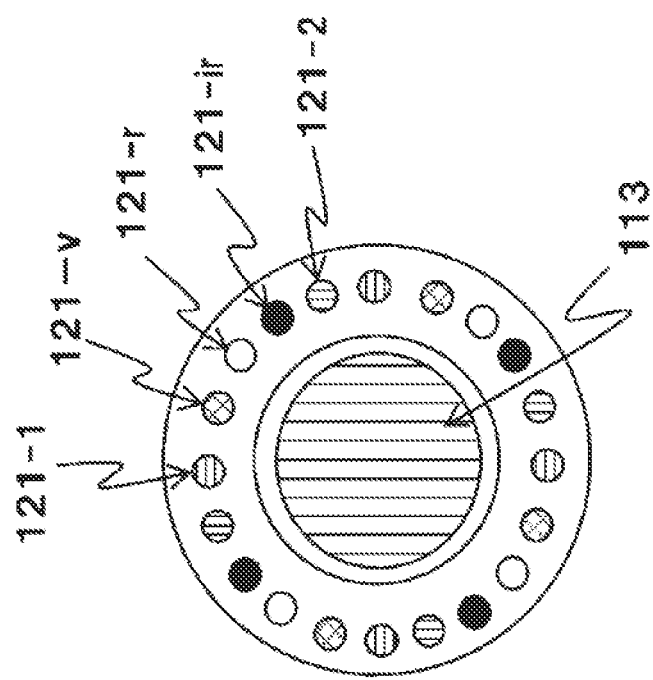
FIG. 12 is a diagram exemplifying light sources of an attachment.

Incidentally, when a scale and brightness of a blemish and those of a pore are similar to each other, it will be difficult to distinguish the blemish from the pore. Accordingly, in a second embodiment, a case will be described in which an analysis of melanin, much of which exists in the portions of the blemishes, is performed and discrimination between the blemishes and the pores is performed using the analysis result. When analysis of melanin is performed, an image is taken after the wavelength of the light source is switched in the imaging device 11 so as to facilitate analysis of melanin. For example, as illustrated in FIG. 12, red LEDs 121-*r* and near infrared LEDs 121-*ir* are further provided in the attachment 12, and the imaging device 11 takes an image of the skin after changing the light source that is used for lighting. Furthermore, in analyzing the melanin, a captured image that has been taken while irradiating ultraviolet rays may be used to perform analysis of the melanin and the melanin analysis may be performed using a spectral reflection factor of the skin. Hereinafter, a case in which analysis of melanin is performed using an image that has been obtained by taking the image while switching between red light and near infrared light will be described.

[3-1. Configuration of Second Embodiment]

Figure 13:
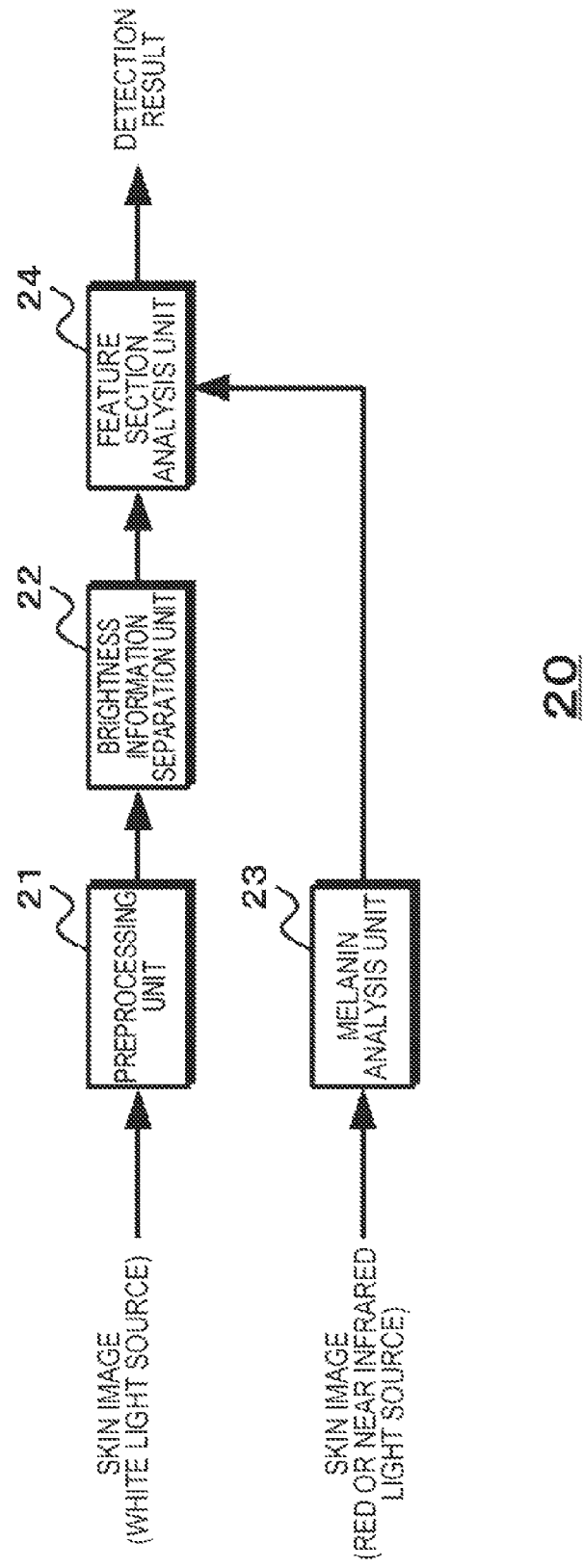
FIG. 13 is a diagram illustrating a configuration of a second embodiment of the image processing apparatus.

FIG. 13 illustrates a configuration of the second embodiment of the image processing apparatus. The image processing apparatus 20 includes the preprocessing unit 21, the brightness information separation unit 22, a melanin analysis unit 23, and the feature section analysis unit 24.

The preprocessing unit 21 acquires a skin image that has been taken with a white light source and preforms preprocessing. Similar to the first embodiment, the preprocessing unit 21 applies contrast enhancement processing to the acquired brightness information of the skin image to emphasize the shadows. Furthermore, when noise stands out, noise removal may be performed before the contrast enhancement, and when shades stand out, shading compensation may be performed before the contrast enhancement. Note that as the brightness information, a blue (B) channel signal is preferably used on a skin image taken with a white light source and a red (R) channel signal is preferably used on a skin image taken with a red light source and a skin image taken with a near infrared light source.

The brightness information separation unit 22 separates the brightness information that has been obtained by the preprocessing unit 21 into global brightness information and local brightness information. In a similar manner to that of the first embodiment, the brightness information separation unit 22 separates the global brightness information, which is information indicating the lighting components included in the image and the structural components of the skin, and the local brightness information, which indicates detailed patterns of the skin, such as texture, from each other.

Figure 14:
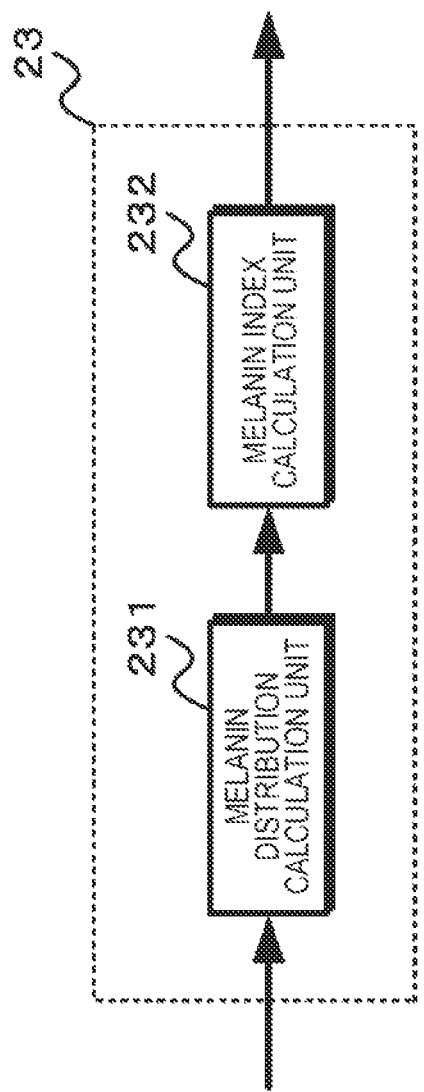
FIG. 14 is a diagram illustrating a configuration of a melanin analysis unit.

The melanin analysis unit 23 acquires both the skin image that has been taken using a red light source and the skin image that has been taken using a near infrared light source and performs analysis of melanin on the basis of the acquired skin images. FIG. 14 illustrates a configuration of the melanin analysis unit 23. The melanin analysis unit 23 includes a melanin distribution calculation unit 231 and a melanin index calculation unit 232.

The melanin distribution calculation unit 231 calculates an average value $Avg_{std}^R$ of a brightness information (red component) $f_{std}^R$ from a captured image that is obtained by irradiating a red light to a standard diffuse reflection plate used to perform calibration (see expression (8)). Similarly, an average value $Avg_{std}^{IR}$ of a brightness information (near infrared component) $f_{std}^{IR}$ is calculated from the captured image that is obtained by irradiating a near infrared light to the standard diffuse reflection plate (see expression (9)).

[Math. 4]

$$Avg_{std}^R = \sum_{x,y} f_{std}^R(x, y) / \sum_{x,y} \qquad (8)$$

$$Avg_{std}^{IR} = \sum_{x,y} f_{std}^{IR}(x, y) / \sum_{x,y} \qquad (9)$$

Subsequently, a melanin distribution Mx is calculated from an input brightness information (red component) $f_{in}^R$ of a captured image that is obtained by irradiating a red light to the skin, an input brightness information (near infrared component) $f_{in}^{IR}$ of a captured image that is obtained by irradiating a near infrared light to the skin, and the average values $Avg_{std}^R$ and $Avg_{std}^{IR}$ when the standard diffuse reflection plate is used (see expression (10)).

[Math. 5]

$$Mx(x, y) = k\left\{\log\left[\frac{f_{in}^R(x, y)}{Avg_{std}^R}\right] - \log\left[\frac{f_{in}^{IR}(x, y)}{Avg_{std}^{IR}}\right]\right\} + q \qquad (10)$$

Note that in expression (10), "k" is a parameter indicating a slope of the expression and "q" is a parameter indicating an intercept of the expression.

The melanin index calculation unit 232 calculates a melanin index by normalizing the melanin distribution that has been calculated by the melanin distribution calculation unit 231.

The melanin index calculation unit 232 calculates an average value $Avg_{in}^R$ of the input brightness information (red component) $f_{in}^R$ and an average value $Avg_{in}^{IR}$ of the input brightness information (near infrared component) $f_{in}^{IR}$ (see expressions (11) and (12)).

[Math. 6]

$$Avg_{in}^R = \sum_{x,y} f_{in}^R(x, y) / \sum_{x,y} \qquad (11)$$

$$Avg_{in}^{IR} = \sum_{x,y} f_{in}^{IR}(x, y) / \sum_{x,y} \qquad (12)$$

Subsequently, an average melanin amount $Mx_{avg}$ is calculated from the average value $Avg_{in}^R$ of the input brightness information (red component) $f_{in}^R$, the average value $Avg_{in}^{IR}$ of the input brightness information (near infrared component) $f_{in}^{IR}$, and the average values $Avg_{std}^R$ and $Avg_{std}^{IR}$ when the standard diffuse reflection had been used (expression (13)).

[Math. 7]

$$Mx_{Avg} = k\left\{\log\left[\frac{Avg_{in}^R}{Avg_{std}^R}\right] - \log\left[\frac{Avg_{in}^{IR}}{Avg_{std}^{IR}}\right]\right\} + q \quad (13)$$

Note that in expression (13), "k" is a parameter indicating a slope of the expression and "q" is a parameter indicating an intercept of the expression.

Subsequently, threshold values Mx_th1 and Mx_th2 are set using the average melanin amount $Mx_{avg}$ (expressions (14) and (15)).

[Math. 8]

$$Mx\_th_1 = Mx_{Avg} - e \quad (14)$$

$$Mx\_th_2 = Mx_{Avg} + e \quad (15)$$

Note that in expressions (14) and (15), "e" is a parameter that defines the melanin distribution Mx that sets the range of the melanin index from "0" to "1". Note that the method of setting the threshold values is not limited to the method described above and, for example, the threshold values may be set as fixed values.

Figure 15:
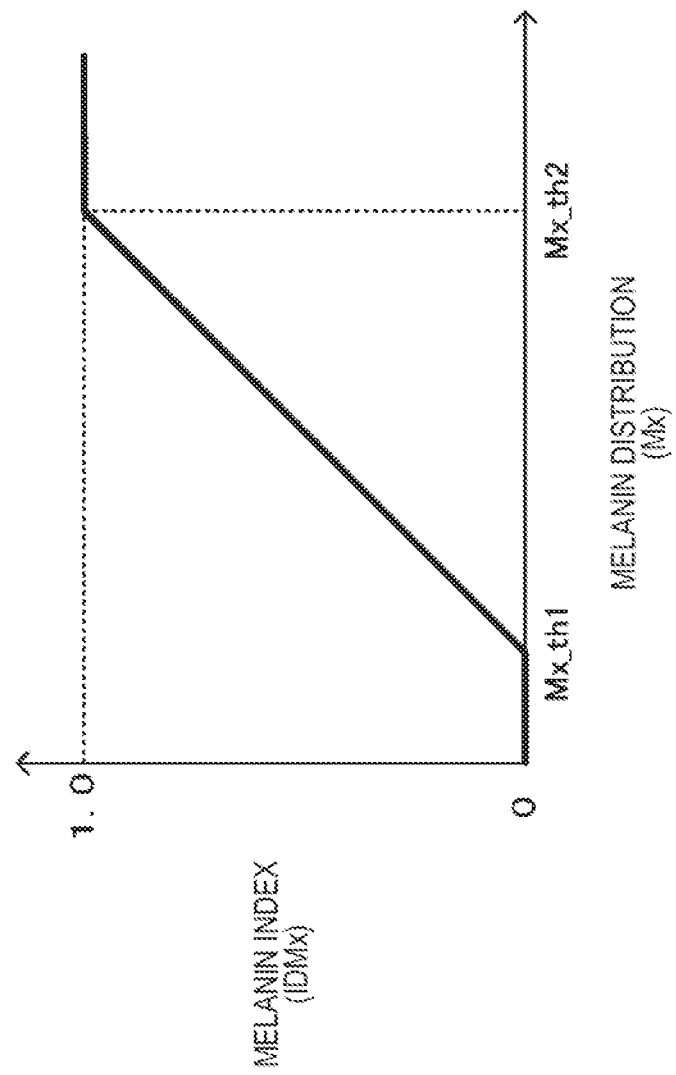
FIG. 15 is a diagram illustrating transfer characteristics that transfers melanin distribution Mx into melanin index $ID_{Mx}$.

The melanin index calculation unit 232 sets the threshold value Mx_th1 and Mx_th2 and, with the transfer characteristics illustrated in FIG. 15, transfers the melanin distribution Mx into a melanin index $ID_{Mx}$.

The feature section analysis unit 24 calculates the feature values from the skin image and, on the basis of the calculated feature values, extracts the feature sections of the skin. Similar to the first embodiment, the feature section analysis unit 24 includes the feature value calculation unit 241, the feature section extraction unit 243, and the statistic calculation unit 244.

The feature value calculation unit 241 calculates the feature values. The feature value calculation unit 241 calculates the feature values using the global brightness information generated in the brightness information separation unit 22, for example. The feature value calculation unit 241 calculates, as feature values, polarities related to gradation of the skin image, and scales indicating pixel areas having pixel values that are similar to each other and that are different from the surroundings of the pixel areas. Furthermore, the feature value calculation unit 241 may further calculate, as feature values, intensities indicating signal differences between the image areas that have pixel values similar to each other and the surroundings of the image areas.

The feature section extraction unit 243 extracts the feature sections on the basis of the feature values that have been obtained by the feature value calculation unit 241. For example, when the pore portions are extracted as the feature sections, the feature section extraction unit 243 sets Laplacian to "1" as the extraction condition. This is because the above matches with the characteristics of the pores since the Lapacian indicates the polarities related to gradation of the skin image and the black pixels are surrounded by the white pixels when the Laplacian is "1". Furthermore, the feature section extraction unit 243 limits the scales that indicate the pixel areas having pixel values that are similar to each other and that are different from the surroundings of the pixel areas. It is known that the size of a pore is about 0.1 mm to 0.3 mm. Accordingly, the feature section extraction unit 243 sets an extraction condition that the scale of the feature values obtained by the feature value calculation unit 241 correspond to the size of the pores.

Furthermore, the feature section extraction unit 243 may limit the intensities. A feature that is considered to be an area where the pores stand out needs a certain amount of signal intensity (contrast difference) with respect to the other areas. Accordingly, the feature section extraction unit 243 sets, as an extraction condition, an intensity (a matrix value) that is capable of extracting pores and the like that stands out.

Incidentally, when the Laplacian is "1", a feature in which the black axles are surrounded by white pixels is indicated. The feature not only matches the features of the pores but also matches the features of the blemishes. Furthermore, when the size and color of a blemish are similar to those of a pore, discrimination of whether the feature section is a pore or a blemish cannot be made. Accordingly, the feature section extraction unit 243 determines, on the basis of the melanin index $ID_{Mx}$ of the extracted feature section, whether the feature section is an area of a pore or an area of a blemish. For example, when the melanin index $ID_{Mx}$ is larger than a predetermined value, the feature section is determined as an area of a pore, and when equivalent or smaller than the predetermined value, the feature section is determined as an area of a blemish.

The static calculation unit 244 calculates statistics of the feature sections that have been extracted by the feature section extraction unit 243. For example, when the pores are extracted as the feature sections while being distinguished from the blemishes, statistic calculation unit 244 measures the number of extracted feature sections and calculates the number of pores. Furthermore, the statistic calculation unit 244 calculates an average value of the scales of the feature sections of the pores to obtain a statistic of the size of the pores from the average value. Furthermore, the statistic calculation unit 244 calculates an average value of the intensities (Hessian value, for example) of the extracted feature sections to set a color density of the pores. Moreover, the statistic calculation unit 244 may obtain a rate of the areas with high melanin index.

The presentation unit 50 that is provided in the imaging device 11, the information processing device 15, or the like presents the analysis result of the feature section analysis unit 24 to a user. For example, the presentation unit 50 displays the statistic that has been calculated in the feature section analysis unit 24 on a screen.

[2. Operation of Second Embodiment]

Figure 16:
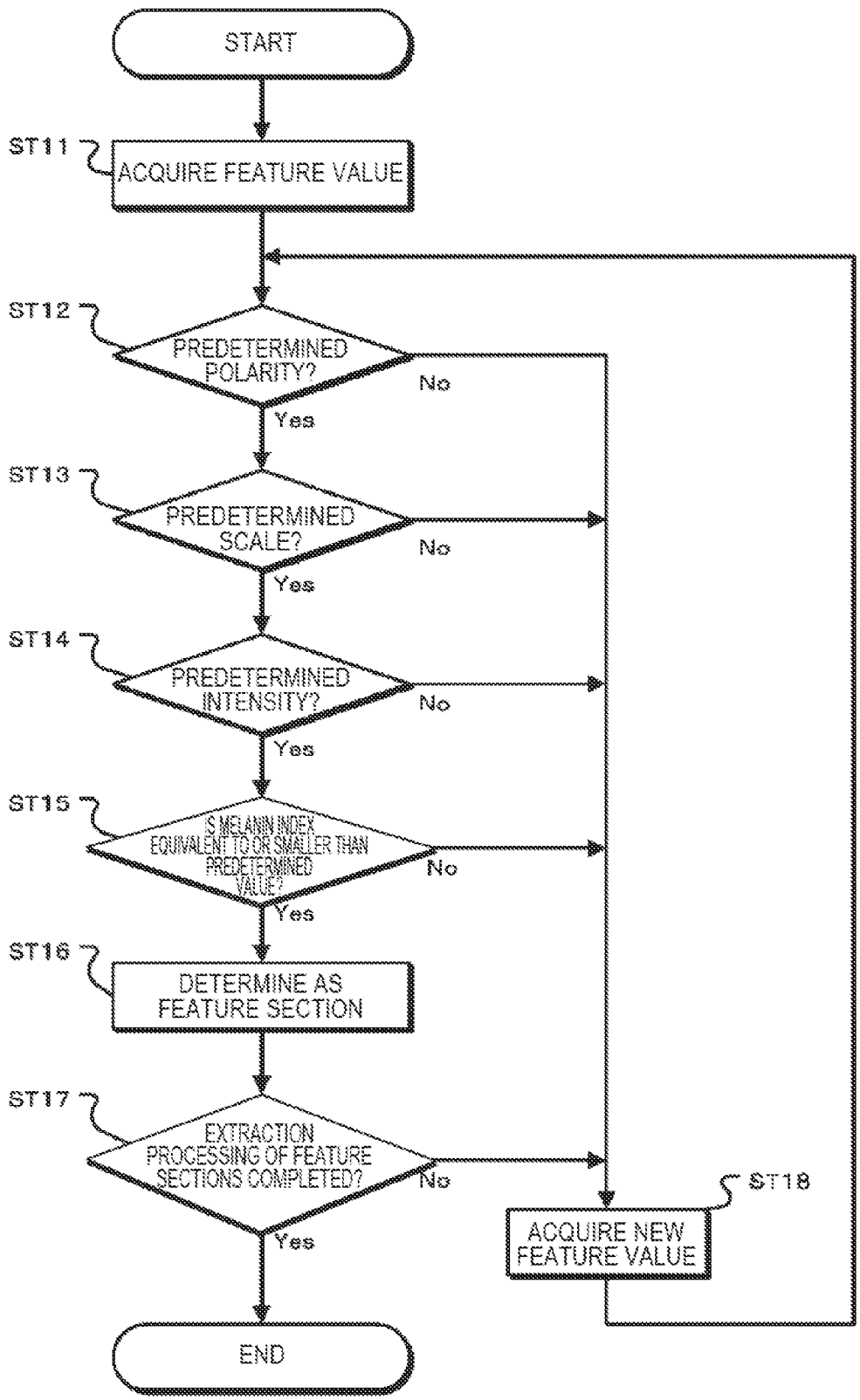
FIG. 16 is a flowchart illustrating an operation extracting the feature sections.

An operation of the second embodiment of the image processing apparatus will be described next. FIG. 16 is a flowchart illustrating an operation extracting the feature sections. In step ST11, the image processing apparatus 20 acquires a feature value. The image processing apparatus 20 acquires a feature value that has been calculated using the brightness information and that indicates, for example, a polarity related to gradation of the skin image, a scale indicating pixel areas having pixel values that are similar to each other and that are different from the surroundings of the pixel areas, and an intensity (a contrast difference), and proceeds to step ST12.

In step ST12, the image processing apparatus 20 discriminates whether the feature value has a predetermined polarity. When the feature value indicates a polarity of the extracted feature sections, for example, when the Laplacian is "1" and the feature value matches the characteristics of the pores or blemishes, then the image processing apparatus 20 proceeds to step ST13. Furthermore, the image processing apparatus 20 proceeds to step ST7 when the feature value does not indicate the polarity of the feature sections.

In step ST13, the image processing apparatus 20 discriminates whether the feature value is of a predetermined scale. When the feature value indicates the scale of the extracted feature sections, for example, when the scales indicated in the feature value is a scale that correspond to the pores, then the image processing apparatus 20 proceeds to step ST14. Furthermore, the image processing apparatus 20 proceeds to step ST18 when the feature value does not indicate the predetermined scale.

In step ST14, the image processing apparatus 20 discriminates whether the feature value has a predetermined intensity. When the feature value indicates the intensity of the extracted feature section, for example, when the intensity indicated in the feature value is an intensity that corresponds to the contrast difference between the pore portions and the skin portion, then the image processing apparatus 20 proceeds to step ST15. Furthermore, when the feature value does not indicate the predetermined intensity, for example, when the intensity indicated in the feature value is lower than the contrast difference between the pore portions and the skin portion, then the image processing apparatus 20 proceeds to step ST18.

In step ST15, the image processing apparatus 20 discriminates whether the melanin index is equivalent to or smaller than a predetermined value. The image processing apparatus 20 proceeds to step ST16 when the melanin index of the feature section is equivalent to or smaller than the predetermined value and proceeds to step ST18 when the melanin index is larger than the predetermined value.

In step ST16, the image processing apparatus 20 discriminates that the feature value is a feature section. For example, when in step ST12 through step ST14, the feature value satisfies the extraction conditions of the pores (blemishes) and when in step ST15, the melanin index is equivalent to or smaller than the predetermined value, the image processing apparatus 20 determines that the feature value is a feature section that indicates a pore and proceeds to step ST17. Note that when the melanin index is larger than the predetermined value, the feature value may be discriminated as a blemish and the process may be proceeded to step ST18.

In step ST17, the image processing apparatus 20 discriminates whether the extraction processing of the feature sections have been completed. If an area of the feature value that has not been determined whether it is a feature section or not remains, the image processing apparatus 20 proceeds to step ST18, and if no such feature value remains, the image processing apparatus 20 ends the operation of extracting the feature sections.

In step ST18, the image processing apparatus 20 acquires a new feature value. The image processing apparatus 20 acquires a feature value that has not been determined whether it is a feature section and returns to step ST12.

Note that in the operation of extracting the feature sections, the order in which the polarities, the scales, and the intensities are determined is not limited to the order illustrated in FIG. 16 but may be ordered in a different manner. Furthermore, the feature sections may be extracted without performing any determination of the intensity.

By performing such processing, the image processing apparatus 20 is made capable of distinguishing the pores from the blemishes and, accordingly, the pores are extracted accurately. Furthermore, when presenting the extraction result of the feature sections on the presentation unit 50, in addition to the first embodiment, the area with high melanin index may be displayed with a different color and the rate of the area with high melanin index that has been obtained by the statistic calculation unit 244 may be displayed.

According to the second embodiment described as above, the pores and the blemishes can be distinguished from each other with the melanin analysis result and the pores can be extracted in an accurate manner. Furthermore, since the pores can be distinguished from the blemishes, the states of the pores and blemishes can be presented in an accurate manner.

<4. Third Embodiment>

While processing that detects the feature sections of the skin has been described in the first embodiment and the second embodiment, it is desirable that discrimination of the change in the feature section of the skin with elapse of time can be made. For example, when a treatment of reducing the size of the pores or treatment and the like of ridding of the pimples and the like is performed, it is desirable that comparison of how the pores and pimples have changed can be performed. Accordingly, in the third embodiment, a description will be given of an image processing apparatus that is capable of positioning an image so that corresponding feature sections are positioned at the same positions in a plurality of skin images of different times.

[4-1. Configuration of Third Embodiment]

Figure 17:
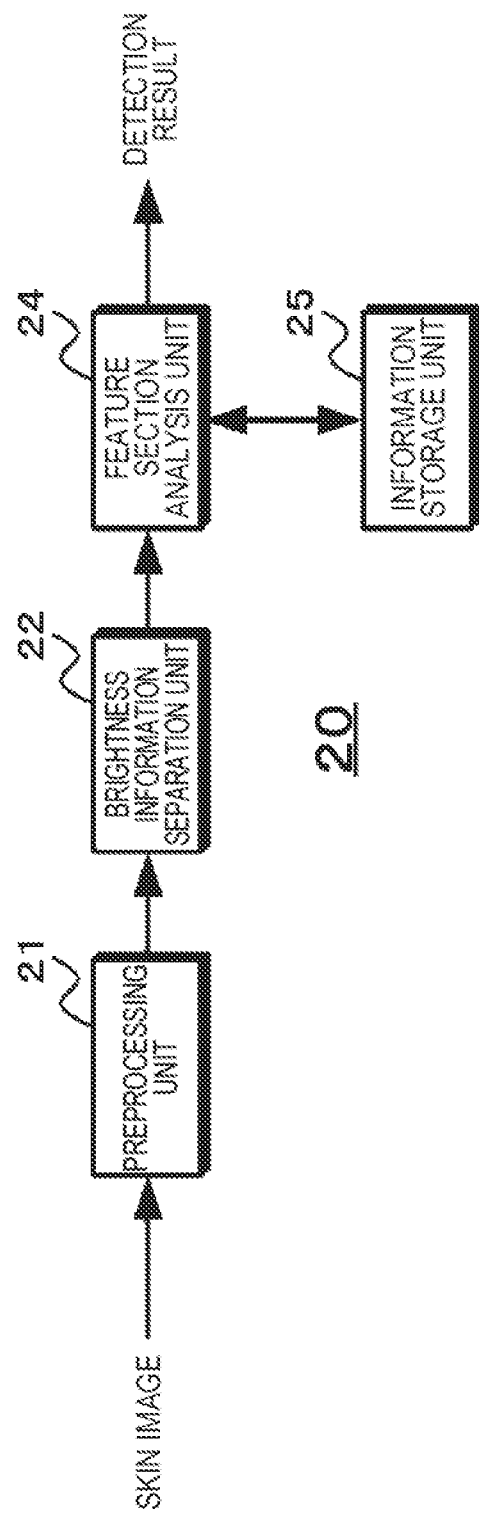
FIG. 17 is a diagram illustrating a configuration of a third embodiment of the image processing apparatus.

FIG. 17 illustrates a configuration of the third embodiment of the image processing apparatus. The image processing apparatus 20 includes the preprocessing unit 21, the brightness information separation unit 22, and the feature section analysis unit 24.

The preprocessing unit 21 acquires a skin image and preforms preprocessing. Similar to the first embodiment, the preprocessing unit 21 applies contrast enhancement processing to the acquired brightness information of the skin image to emphasize the shadows. Furthermore, when noise stands out, noise removal may be performed before the contrast enhancement, and when shades stand out, shading compensation may be performed before the contrast enhancement.

The brightness information separation unit 22 separates the brightness information that has been obtained by the preprocessing unit 21 into global brightness information and local brightness information. In a similar manner to that of the first embodiment, the brightness information separation unit 22 separates the global brightness information, which is information indicating the lighting components included in the image and the structural components of the skin, and the local brightness information, which indicates detailed patterns of the skin, such as texture, from each other.

Figure 18:
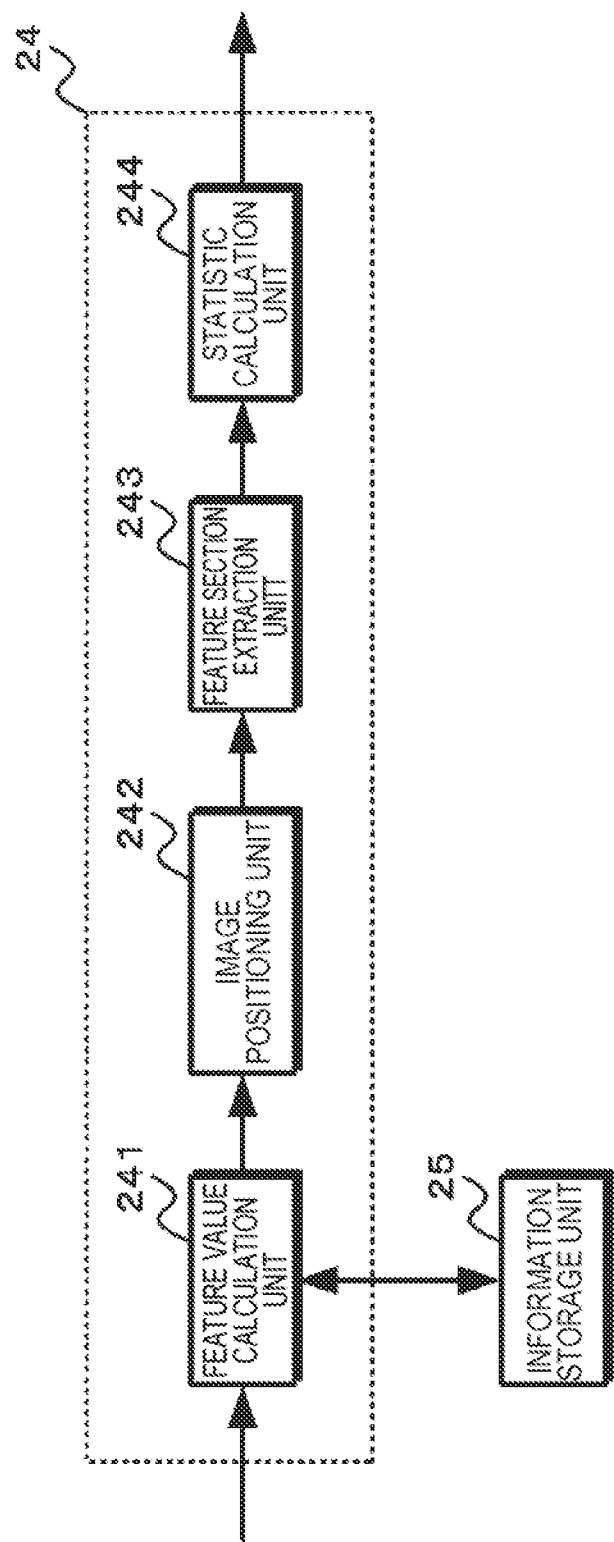
FIG. 18 is a diagram illustrating a configuration of a feature section analysis unit.

The feature section analysis unit 24 calculates the feature values from the skin image and, on the basis of the calculated feature values, analyzes the feature sections of the skin. As illustrated in FIG. 18, the feature section analysis unit 24 includes the feature value calculation unit 241, a positioning unit 242, the feature section extraction unit 243, and the statistic calculation unit 244.

The feature value calculation unit 241 calculates the feature values. The feature value calculation unit 241 calculates the feature values using the global brightness information generated in the brightness information separation unit 22, for example. The feature value calculation unit 241 calculates, as feature values, polarities related to gradation of the skin image, and scales indicating pixel areas having pixel values that are similar to each other and that are different from the surroundings of the pixel areas. Furthermore, the feature value calculation unit 241 may further calculate, as feature values, intensities indicating signal differences between the image areas that have pixel values similar to each other and the surroundings of the image areas.

Furthermore, the feature value calculation unit 241 calculates second feature values used to match the feature sections in order to match the position of the skin image of the past and the position of the skin image of the present to each other. The feature value calculation unit 241 calculates, as the second feature values, feature values that indicate polarities of the intensity change, for example.

Calculation of the second feature values that indicate the polarities of the intensity change will be exemplified next. The feature value calculation unit 241 obtains an orientation (=reference angle) of each feature section. For example, filtering processing with the Haar wavelet (4s) is performed in a range of radius 6s around a feature section (x, y, s)) and the responses (dx and dy) in x direction and y direction are obtained to calculate a gradient direction θ and an intensity m (see expressions (16) and (17)). Note that "s" indicates the scale.

[Math. 9]

$$\theta(x, y) = \tan^{-1}\left(\frac{dx}{dy}\right) \quad (16)$$

$$m(x, y) = \sqrt{dx^2 + dy^2} \quad (17)$$

Subsequently, a histogram of gradient directions based on a resolution is formed. For example, when the resolution is set at "bin width=60 degrees", a histogram with classes in six directions will be formed. A class value is set in each class by summing the intensities of the gradient direction included in the class. In the histogram formed in the above manner, the direction in which the class value is the largest is set as the orientation.

Subsequently, a square area, for example, a "20s×20s" area, centering around a feature section is divided into "4×4" sub-areas and is rotated by the angle of the orientation. Then after, each of the sub-areas is divided into four to form a Haar Wavelet (2s) with the same size so as to obtain a gradient vector. Four-dimensional vectors (Σdx, Σdy, Σ|dx|, and Σ|dy|) are calculated from "dx" and "dy" that are a component in the x direction and a component in the y direction, respectively, of the gradient vector. The four-dimensional vectors have large gradients in the x direction and the gradient directions are positive when the absolute values thereof are large. Furthermore, when the gradient directions are negative, gradients in the x direction are small and the absolute values thereof are large. As described above, the four-dimensional vectors become information that indicates the polarities of the intensity change. Accordingly, the four-dimensional vectors are obtained from the 16 sub-areas, and 64 feature values are used as the second feature values.

Furthermore, the feature value calculation unit 241 stores the global brightness information and the second feature values that have been calculated from the global brightness information so as to allow the position to be matched with the skin image that is taken subsequently.

An information storage unit 25 stores the global brightness information and the second feature values that have been calculated from the global brightness information. Note that the skin image, the skin image after preprocessing, or the global brightness information may be stored in the information storage unit 25 and processing as described above may be performed in the feature value calculation unit 241 and the like to calculate the second feature values, and the calculated second feature values may be output to the positioning unit 242.

The positioning unit 242 performs matching between the skin image of the past and the skin image of the present and detects pairs of feature sections that correspond to each other. As for the matching method, a method such as a linear search of the nearest neighbor may be adopted.

Furthermore, when more than a predetermined number of pairs of feature sections are found, the positioning unit 242 performs projective transformation and the like and matches the positions of the new skin image and the skin image of the past. For example, by obtaining a homography matrix from the pairs of feature sections and by performing projective transformation, the position of the new skin image is matched with the position of the skin image of the past. Furthermore, when the number of pairs of feature sections that have been found through matching is equivalent to or smaller than the predetermined number, the positioning unit 242 presents a piece of advice, on the basis of the positions of the paired portions of the feature points, to move the imaging area in a direction in which more pairs of feature sections can be found. For example, when the position of the corresponding feature sections of the new skin image is biased to the left of the display with respect to the position of the skin image of the past, a piece of advice is presented to move the imaging area to the left so that the position of the corresponding feature sections of the skin image of the past and those of the skin image of the present are at similar positions.

The feature section extraction unit 243 extracts the feature sections on the basis of the feature values that have been obtained by the feature value calculation unit 241. For example, when the pore portions are extracted as the feature sections, the feature section extraction unit 243 sets Laplacian to "1" as the extraction condition. This is because the above matches with the characteristics of the pores since the Lapacian indicates the polarities related to gradation of the skin image and the black pixels are surrounded by the white pixels when the Laplacian is "1". Furthermore, the feature section extraction unit 243 limits the scales that indicate the pixel areas having pixel values that are similar to each other and that are different from the surroundings of the pixel areas. It is known that the size of a pore is about 0.1 mm to 0.3 mm. Accordingly, the feature section extraction unit 243 sets an extraction condition that the scale of the feature values obtained by the feature value calculation unit 241 correspond to the size of the pores.

Furthermore, the feature section extraction unit 243 may limit the intensities. A feature that is considered to be an area where the pores stand out needs a certain amount of signal intensity (contrast difference) with respect to the other areas. Accordingly, the feature section extraction unit 243 sets, as an extraction condition, an intensity (a matrix value) that is capable of extracting pores and the like that stands out.

By extracting the feature points that satisfy all of the extraction conditions that are set as above as the feature sections of the skin, the feature section extraction unit 243 will be capable of extracting only the pore areas from the skin image. Note that as described later, the extraction conditions may be changed to extract pimples and the like as feature sections of the skin.

As described above, the feature section extraction unit 243 extracts the feature sections of the pores, pimples, and the like of the skin by extracting feature points with the polarities related to gradation of the skin image and the scales.

The static calculation unit 244 calculates statistics of the feature sections that have been extracted by the feature section extraction unit 243. For example, when the pores are extracted as the feature sections, statistic calculation unit 244 measures the number of extracted feature sections and calculates the number of pores. Furthermore, the statistic calculation unit 244 calculates an average value of the scales of the extracted feature sections to obtain a statistic of the size of the pores from the average value. Furthermore, the statistic calculation unit 244 calculates an average value of the intensities (Hessian value, for example) of the extracted feature sections to set a color density of the pores.

The presentation unit 50 that is provided in the imaging device 11, the information processing device 15, or the like presents the analysis result of the feature section analysis unit 24 to a user. For example, the presentation unit 50 displays the statistic that has been calculated in the feature section analysis unit 24 on a screen.

[4-2. Operation of Third Embodiment]

Figure 19:
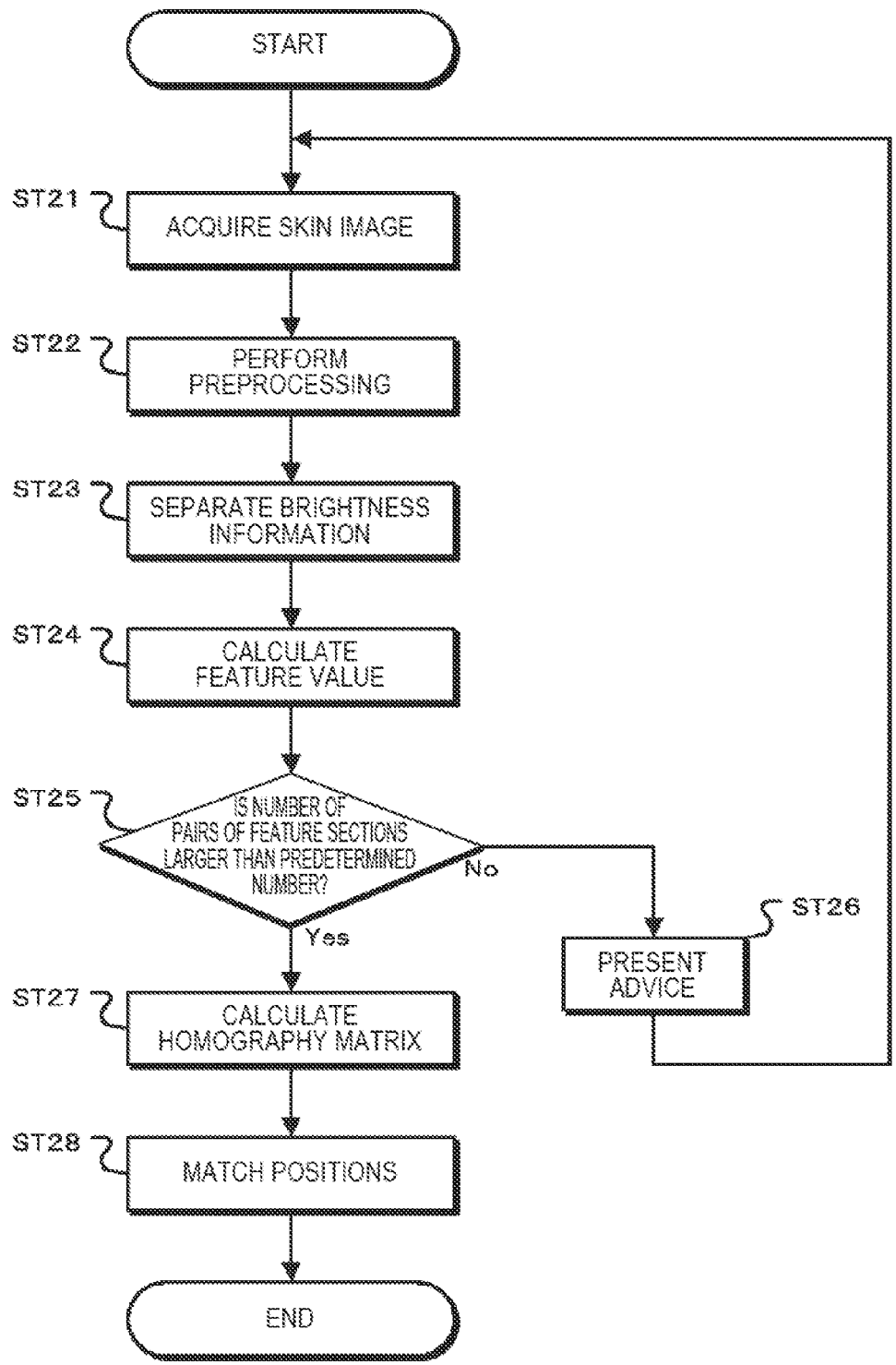
FIG. 19 is a flowchart illustrating an operation of the third embodiment.

An operation of the third embodiment of the image processing apparatus will be described next. FIG. 19 is a flowchart illustrating an operation of the third embodiment. In step ST21, the image processing apparatus 20 acquires a skin image. The image processing apparatus 20 acquires the skin image generated by the imaging device 11 and proceeds to step ST22.

In step ST22, the image processing apparatus 20 performs preprocessing. The image processing apparatus 20 performs contrast enhancement processing and the like to the brightness information of the acquired skin image to greatly emphasize the shadows and proceeds to step ST23.

In step ST23, the image processing apparatus 20 separates the brightness information. The image processing apparatus 20 separates the brightness information, on which preprocessing has been performed, into global brightness information and local brightness information and proceeds to step ST24.

In step ST24, the image processing apparatus 20 calculates the feature values. The image processing apparatus 20 using the global brightness information calculates polarities related to gradation of the skin image and scales indicating pixel areas having pixel values that are similar to each other and that are different from the surroundings of the pixel areas as feature values, and proceeds to step ST25. Furthermore, the image processing apparatus 20 may further calculate intensities indicating signal differences between the image areas that have pixel values similar to each other and the surroundings of the image areas.

In step ST25, the image processing apparatus 20 discriminates whether the number of pairs of feature sections is larger than a predetermined number. The image processing apparatus 20 discriminates whether the number of pairs of a feature section that has been detected from the skin image of the past and a corresponding feature section of the skin image of the present are larger than the predetermined number, and when the number is equivalent to or smaller than the predetermined number, the image processing apparatus 20 proceeds to step ST26 and when the number is larger than the predetermined number, proceeds to step ST27.

In step ST26, the image processing apparatus 20 presents a piece of advice. The image processing apparatus 20 presents a piece of advice, such as a moving direction of the imaging area, on the presentation unit 50 so that the positions of the pairs of feature sections in the skin image of the past and those in the skin image generated by the imaging device 11 are positioned at substantially the same position, and then returns to step ST21.

In step ST27, the image processing apparatus 20 calculates a homography matrix. In order to match the positions of the skin image of the past and the skin image generated by the image device 11, the image processing apparatus 20 calculates a homography matrix that indicates the positional correspondence between the skin image of the past and the skin image generated by the imaging device 11, and proceeds to step ST28.

In step ST28, the image processing apparatus 20 performs positioning. The image processing apparatus 20 performance projective transformation using the calculated homography matrix to match the positions of the skin image of the past and the skin image generated by the imaging device 11, and ends the process.

Performing the process described above, the image processing apparatus 20 performs matching of the positions of the images and presents the detection result so that the corresponding feature sections of the skin image of the past and those of the skin image generated by the imaging device 11 can be easily compared.

Figure 20:
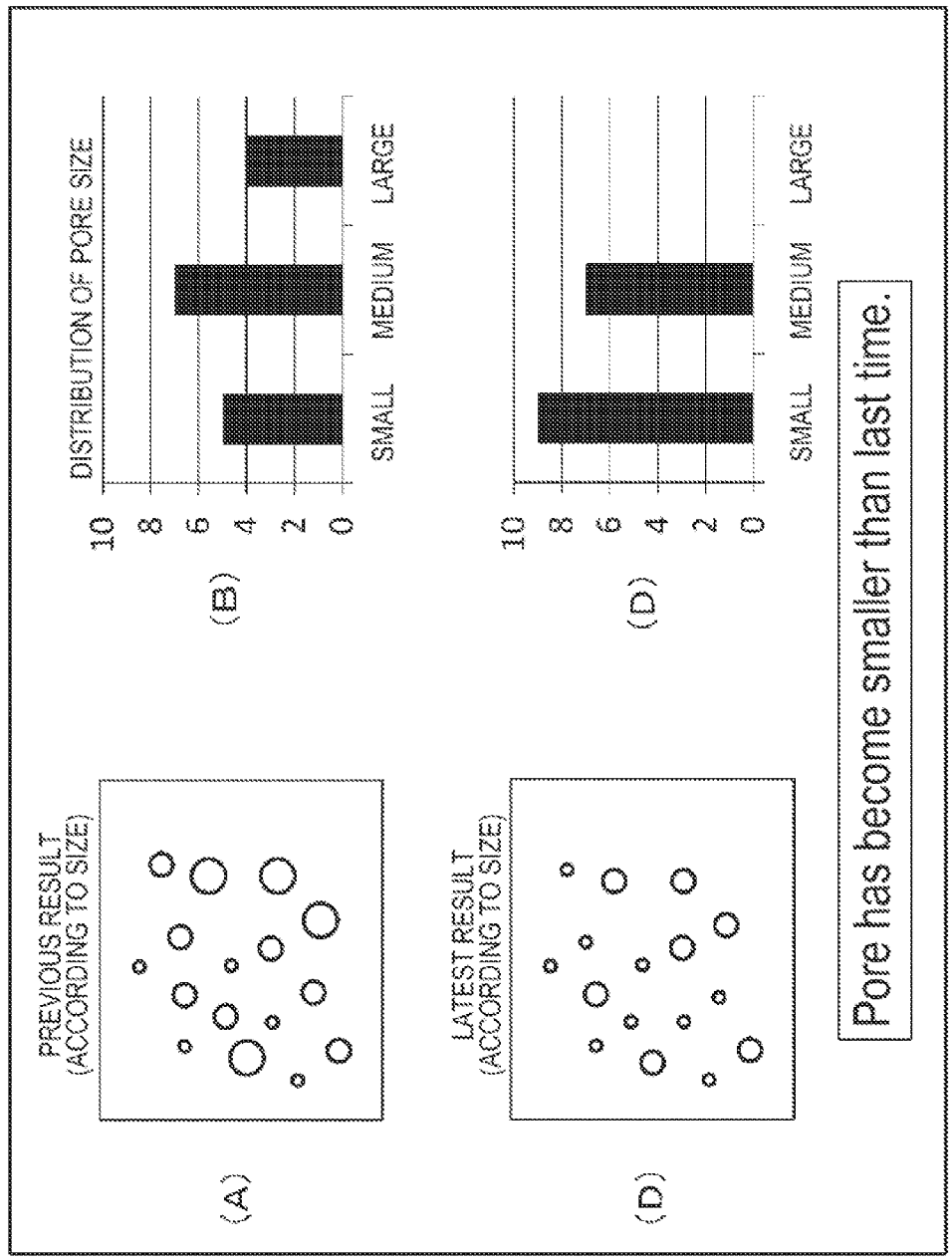
FIG. 20 is a diagram exemplifying an operation of a presentation unit.

FIG. 20 exemplifies an operation of the presentation unit. FIG. 20(A) illustrates a state in which pores are plotted on the skin image of the past according to their sizes, for example, and FIG. 20(B) is a distribution (a histogram) of the sizes of the pores of the skin image of the past displayed according to their sizes. FIG. 20(C) illustrates a state in which pores are plotted on the skin image, which has been newly generated by the imaging device, according to their sizes, for example, and FIG. 20(D) is a distribution (a histogram) of the sizes of the pores of the skin image, which has been newly generated, displayed according to their sizes. Furthermore, changes from before may be presented to the user. For example, in FIG. 20, a message indicating that the overall number of pores has become smaller compared to before is displayed. Note that in the embodiment, while the sizes of the pores have been compared, the number of pores or the color densities of the pores may be compared, or all of the above may be compared.

As described above, since matching of the positions of the skin image of the past and the skin image of the present are performed and since the detection result of the feature sections are displayed, it will be easy to confirm temporal change of the feature sections.

Figure 21:
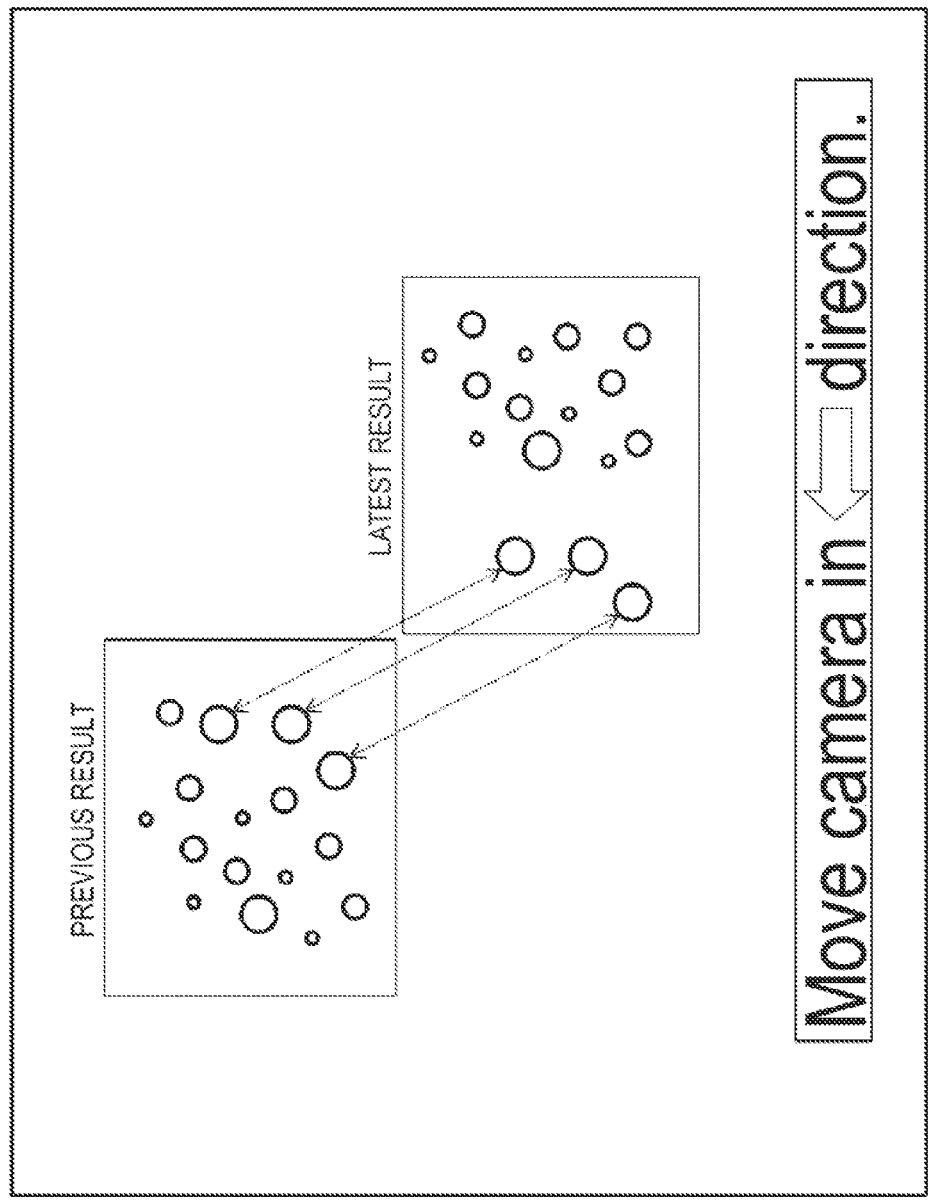
FIG. 21 exemplifies a piece of advice given when the number of pairs of feature sections is equivalent to or smaller than a predetermined number.

FIG. 21 exemplifies a piece of advice given when the number of pairs of feature sections is equivalent to or smaller than a predetermined number. In presenting the advice, for example, the detection result of the skin image of the past and the detection result of the new skin image are displayed, and, further, a piece of advice on a moving direction of the imaging area that positions the skin images at substantially the same position is given. Accordingly, matching the position of the skin image of the past and that of the skin image of the present can be easily performed.

According to the third embodiment described as above, the skin condition of the past and the skin condition of the present can be compared easily; accordingly, it is possible to the check, with ease and with precision, what kind of effects have been obtained from the various pieces of advice and the like.

The processing sequence that is explained in the specification can be implemented by hardware, by software and by a configuration that combines hardware and software. In a case where the processing is implemented by software, it is possible to install in memory within a computer that is incorporated into dedicated hardware a program in which the processing sequence is encoded and to execute the program. It is also possible to install a program in a general-purpose computer that is capable of performing various types of processing and to execute the program.

For example, the program can be recorded on a hard disk or ROM (Read Only Memory) as a recording medium in advance. Alternatively, the program can be temporarily or permanently stored (recorded) in (on) a removable recording medium such as a flexible disk, CD-ROM (Compact Disc Read Only Memory), MO (Magneto Optical) disk, DVD (Digital Versatile Disc), a magnetic disk, or a semiconductor memory card. Such a removable recording medium can be provided as so-called package software.

In addition, the program can be, not only installed on a computer from a removable recording medium, but also transferred wirelessly or by wire to the computer from a download site via a network such as a LAN (Local Area Network) or the Internet. In such a computer, a program transferred in the aforementioned manner can be received and installed on a recording medium such as built-in hardware.

Note that the present technique should not be interpreted to be limited to the embodiments of the technique described above. The embodiments of the technique are disclosed in an exemplifying manner and it is obvious that those skilled in the art can modify or replace the embodiments without departing from the scope of the technique. In other words, the claims should be taken into account in understanding the scope of the present technique.

(1)

An image processing apparatus, including:

a feature value calculation unit configured to calculate, as feature values, a polarity related to gradation of a skin image and a scale indicating image areas each having a pixel value that is similar to each other and that are different from surroundings of the image areas; and a feature section extraction unit configured to extract a feature section of the skin image on a basis of the feature values calculated by the feature value calculation unit.

(2)

The image processing apparatus according to (1), further including:

a brightness information separation unit configured to perform brightness information separation processing on the skin image so as to acquire global brightness information, wherein the feature value calculation unit calculates the feature values with the global brightness information acquired by the brightness information separation unit.

(3)

The image processing apparatus according to (1) or (2), wherein the feature value calculation unit calculates, as the feature values, intensities indicating signal differences between the image areas each having a pixel value that is similar to each other and the surroundings.

(4)

The image processing apparatus according to any one of (1) to (3), further including:

a melanin analysis unit configured to analyze melanin, wherein the feature section extraction unit extracts a feature section using the feature values calculated by the feature value calculation unit and an analysis result obtained by the melanin analysis unit.

(5)

The image processing apparatus according to any one of (1) to (4), further including:

an image positioning unit configured to match positions of first and second skin images in a manner that feature sections are consistent with each other, wherein the feature value calculation unit calculates a second feature value that indicates a polarity of an intensity change, and wherein the image positioning unit matches the positions of the skin images by performing matching of the feature sections using the second feature value in a manner that corresponding feature sections of the first and second skin images are consistent with each other.

(6)

The image processing apparatus according to (5), wherein an image of the past is used as the first skin image and an image of the present is used as the second skin image, wherein when the number of corresponding feature sections is equivalent to or smaller than a predetermined number, the image positioning unit presents a piece of advice on moving an imaging area in a manner that a position of the corresponding feature section of the second skin image is positioned at a position of the corresponding feature section of the first skin image.

(7)

The image processing apparatus according to any one of (1) to (6), wherein the feature section extraction unit extracts, as the feature section, at least one of pores, pimples, blemishes, and impurities in pores.

(8)

The image processing apparatus according to (7), wherein the feature section extraction unit extracts at least one of the pores, the pimples, and the blemishes on a basis of feature values calculated by the feature value calculation unit from a skin image taken using white light, and extracts the impurities in pores on a basis of feature values calculated by the feature value calculation unit from a skin image taken using near-ultraviolet light.

(9)

The image processing apparatus according to any one of (1) to (8), further including:

a statistic calculation unit configured to generate information related to at least one of numbers, sizes, and color densities of feature sections by calculating a statistic on a basis of an extraction result of the feature sections having feature values satisfying an extraction condition set in advance.

(10)

The image processing apparatus according to any one of (1) to (9), wherein the skin image is an image in which a surface reflection of the skin has been removed by configuring a light source and a polarizing filter provided on an imagining unit to have an orthogonal relationship with each other.

INDUSTRIAL APPLICABILITY

In the image processing apparatus, the image processing method, the program, and the image processing system of the present technology, polarities related to gradation of a skin image and scales indicating image areas having pixel values that are similar to each other and that are different from the surroundings of the pixel areas are calculated as feature values, and on the basis of the feature values, feature sections of the skin image are extracted. Accordingly, pores, pimples, and the like of the skin can be accurately detected as the feature sections and various pieces of advice and the like can be given in an appropriate manner in accordance with the skin condition. Therefore, the present technique is suitable for electronic devices that include an imaging function of the skin, such as, for example, digital cameras, portable terminal devices, and information processing devices and the like that provide various services through a network and the like.

REFERENCE SIGNS LIST 10 image processing system
11 imaging device
12 attachment
15, 16 information processing device
20 image processing apparatus
21 preprocessing unit
22 brightness information separation unit
23 melanin analysis unit
24 feature section analysis unit
25 information storage unit
50 presentation unit
111 lens barrel
112 imaging unit
113 polarizing filter
121 light source
231 melanin distribution calculation unit
232 melanin index calculation unit
241 feature value calculation unit
242 positioning unit
243 feature section extraction unit
244 statistic calculation unit

The invention claimed is:

1. An image processing apparatus, comprising:
a feature value calculation unit configured to calculate, as feature values, a polarity related to gradation of a skin image and a scale indicating image areas each having a pixel value that is similar to each other and that are different from surroundings of the image areas; and
a feature section extraction unit configured to extract a feature section of the skin image on a basis of the feature values calculated by the feature value calculation unit such that the feature section is extracted when the polarity calculated by the feature value calculation unit has a predetermined polarity and the scale calculated by the feature value calculation unit has a predetermined scale value.

2. The image processing apparatus according to claim 1, further comprising:
a brightness information separation unit configured to perform brightness information separation processing on the skin image so as to acquire global brightness information,
wherein the feature value calculation unit calculates the feature values with the global brightness information acquired by the brightness information separation unit.

3. The image processing apparatus according to claim 1, wherein the feature value calculation unit calculates, as the feature values, intensities indicating signal differences between the image areas each having a pixel value that is similar to each other and the surroundings.

4. The image processing apparatus according to claim 1, further comprising:
a melanin analysis unit configured to analyze melanin, wherein the feature section extraction unit extracts a feature section using the feature values calculated by the feature value calculation unit and an analysis result obtained by the melanin analysis unit.

5. The image processing apparatus according to claim 1, wherein the feature section extraction unit extracts, as the feature section, at least one of pores, pimples, blemishes, and impurities in pores.

6. The image processing apparatus according to claim 1, further comprising:
a statistic calculation unit configured to generate information related to at least one of numbers, sizes, and color densities of feature sections by calculating a statistic on a basis of an extraction result of the feature sections having feature values satisfying an extraction condition set in advance.

7. An image processing apparatus, comprising:
a feature value calculation unit configured to calculate, as feature values, a polarity related to gradation of a skin image and a scale indicating image areas each having a pixel value that is similar to each other and that are different from surroundings of the image areas;
a feature section extraction unit configured to extract a feature section of the skin image on a basis of the feature values calculated by the feature value calculation unit; and
an image positioning unit configured to match positions of first and second skin images in a manner that feature sections are consistent with each other,
wherein the feature value calculation unit calculates a second feature value that indicates a polarity of an intensity change, and
wherein the image positioning unit matches the positions of the skin images by performing matching of the feature sections using the second feature value in a manner that corresponding feature sections of the first and second skin images are consistent with each other.

8. The image processing apparatus according to claim 7, wherein an image of the past is used as the first skin image and an image of the present is used as the second skin image,
wherein when the number of corresponding feature sections is equivalent to or smaller than a predetermined number, the image positioning unit presents a piece of advice on moving an imaging area in a manner that a position of the corresponding feature section of the second skin image is positioned at a position of the corresponding feature section of the first skin image.

9. An image processing apparatus, comprising:
a feature value calculation unit configured to calculate, as feature values, a polarity related to gradation of a skin image and a scale indicating image areas each having a pixel value that is similar to each other and that are different from surroundings of the image areas; and
a feature section extraction unit configured to extract a feature section of the skin image on a basis of the feature values calculated by the feature value calculation unit,
wherein the feature section extraction unit extracts, as the feature section, at least one of pores, pimples, blemishes, and impurities in pores, and
wherein the feature section extraction unit extracts at least one of the pores, the pimples, and the blemishes on a basis of feature values calculated by the feature value calculation unit from a skin image taken using white light, and extracts the impurities in pores on a basis of feature values calculated by the feature value calculation unit from a skin image taken using near-ultraviolet light.

10. An image processing apparatus, comprising:
a feature value calculation unit configured to calculate, as feature values, a polarity related to gradation of a skin image and a scale indicating image areas each having a pixel value that is similar to each other and that are different from surroundings of the image areas; and
a feature section extraction unit configured to extract a feature section of the skin image on a basis of the feature values calculated by the feature value calculation unit,
wherein the skin image is an image in which a surface reflection of the skin has been removed by configuring a light source and a polarizing filter provided on an imagining unit to have an orthogonal relationship with each other.

11. An image processing method, comprising the steps of:
calculating, as feature values, a polarity related to gradation of a skin image and a scale indicating image areas each having a pixel value that is similar to each other and that are different from surroundings of the image areas; and
extracting a feature section of the skin image on a basis of the calculated feature values such that the feature section is extracted when the polarity calculated by the feature value calculation unit has a predetermined polarity and the scale calculated by the feature value calculation unit has a predetermined scale value.

12. A non-transitory computer readable medium having stored thereon a program when executed causes a computer to execute a skin image processing method, the method comprising:
calculating, as feature values, a polarity related to gradation of a skin image and a scale indicating image areas each having a pixel value that is similar to each other and that are different from surroundings of the image areas; and
extracting a feature section of the skin image on a basis of the calculated feature values such that the feature section is extracted when the polarity calculated by the feature value calculation unit has a predetermined polarity and the scale calculated by the feature value calculation unit has a predetermined scale value.

13. An image processing system, comprising:
an imaging device; and
an information device,
wherein the imaging device is provided with an imaging unit configured to generate a skin image, and
wherein one of the imaging device and information processing device is provided with
a feature value calculation unit configured to calculate, as feature values, a polarity related to gradation of a skin image and a scale indicating image areas each having a pixel value that is similar to each other and that are different from surroundings of the image areas,
a feature section extraction unit configured to extract a feature section of the skin image on a basis of the feature values calculated by the feature value calculation unit such that the feature section is extracted when the polarity calculated by the feature value calculation unit has a predetermined polarity and the scale calculated by the feature value calculation unit has a predetermined scale value, and
a presentation unit configured to present an extraction result of the feature section.

* * * * *